(12) United States Patent
Portney

(10) Patent No.: US 6,918,930 B2
(45) Date of Patent: *Jul. 19, 2005

(54) IRIS FIXATED INTRAOCULAR LENS SUITABLE FOR USE WITH ATTACHING INSTRUMENT

(76) Inventor: Valdemar Portney, 11940 N. Riviera, Tustin, CA (US) 92782

(*) Notice: Subject to any disclaimer, the term of this patent is extended or adjusted under 35 U.S.C. 154(b) by 0 days.

This patent is subject to a terminal disclaimer.

(21) Appl. No.: 10/058,592

(22) Filed: Jan. 28, 2002

(65) Prior Publication Data

US 2002/0116062 A1 Aug. 22, 2002

Related U.S. Application Data

(63) Continuation-in-part of application No. 09/489,069, filed on Jan. 21, 2000, now Pat. No. 6,342,058, which is a continuation-in-part of application No. 09/312,566, filed on May 14, 1999, now Pat. No. 6,152,959.

(51) Int. Cl.[7] ............................................. A61F 2/16
(52) U.S. Cl. ..................................... 623/6.47; 623/6.36
(58) Field of Search ............................... 623/6.11, 6.13, 623/6.15, 6.18, 6.19, 6.22, 6.32–6.55, 6.59

(56) References Cited

U.S. PATENT DOCUMENTS

| | | | |
|---|---|---|---|
| 3,989,049 A | 11/1976 | Yoon | |
| 4,435,855 A | 3/1984 | Pannu | |
| 4,542,540 A | 9/1985 | White | |
| 4,542,541 A | 9/1985 | Pannu | |
| RE32,525 E | 10/1987 | Pannu | |
| 4,706,666 A | 11/1987 | Sheets | |
| 5,135,530 A | 8/1992 | Lehmer | |
| 5,192,319 A | 3/1993 | Worst | |
| 5,222,960 A | 6/1993 | Poley | |
| 5,395,378 A | 3/1995 | McDonald | |
| 5,618,307 A | 4/1997 | Donlon et al. | |
| 6,152,959 A | 11/2000 | Portney | |
| 6,197,059 B1 * | 3/2001 | Cumming | 623/6.39 |
| 6,342,058 B1 | 1/2002 | Portney | |
| 6,395,028 B1 * | 5/2002 | Tran et al. | 623/6.44 |

FOREIGN PATENT DOCUMENTS

| | | | |
|---|---|---|---|
| WO | WO 99/62434 A1 * | 12/1999 | A61F/2/16 |
| WO | WO 00/74601 A1 * | 12/2000 | A61F/2/16 |

* cited by examiner

*Primary Examiner*—David H. Willse
(74) *Attorney, Agent, or Firm*—Denton L. Anderson; Sheldon & Mak

(57) ABSTRACT

An intraocular lens has an optic and two fixation members. Each fixation member has at least one connecting element and a pincer element. The pincer element has a side region with a central portion and opposed end portions. The pincer element further has a pair of pincer arms attached end-to-end from respective opposed end portions of the side region. In one embodiment, the side region has a first location disposed closer to the optic than the pincer gap and a second side region disposed further from the optic than the pincer gap. The distance of both side regions to the central-most portion of the pincer gap is substantially identical.

6 Claims, 22 Drawing Sheets

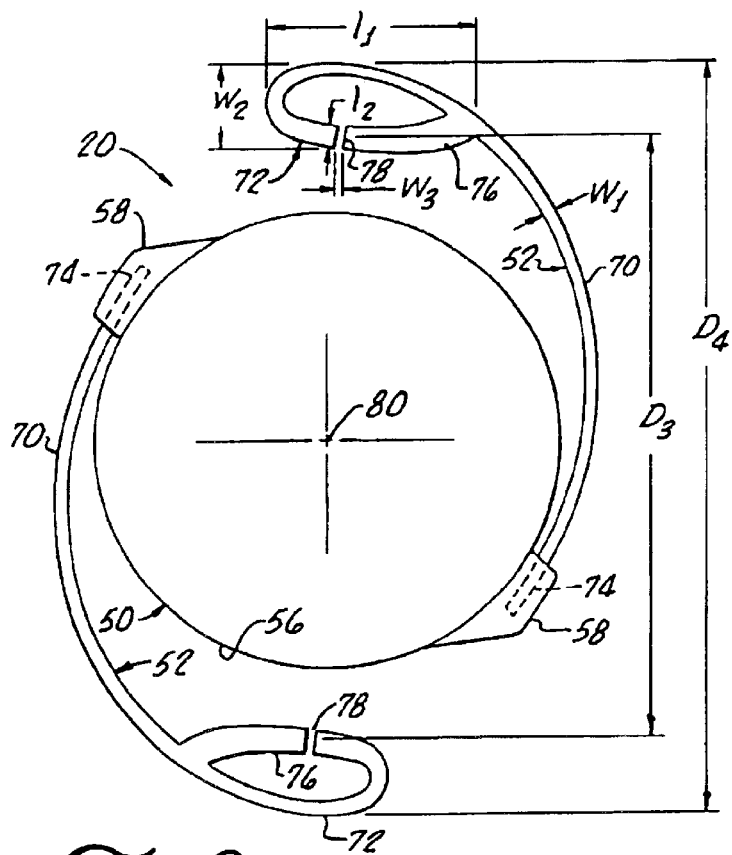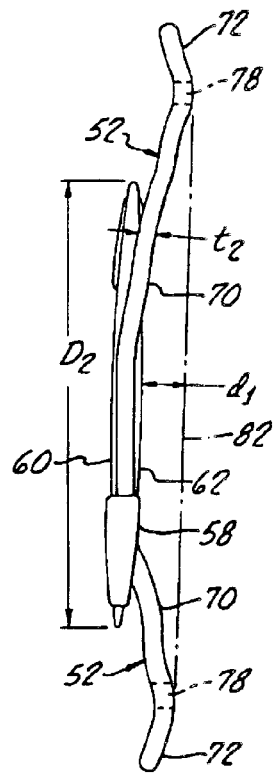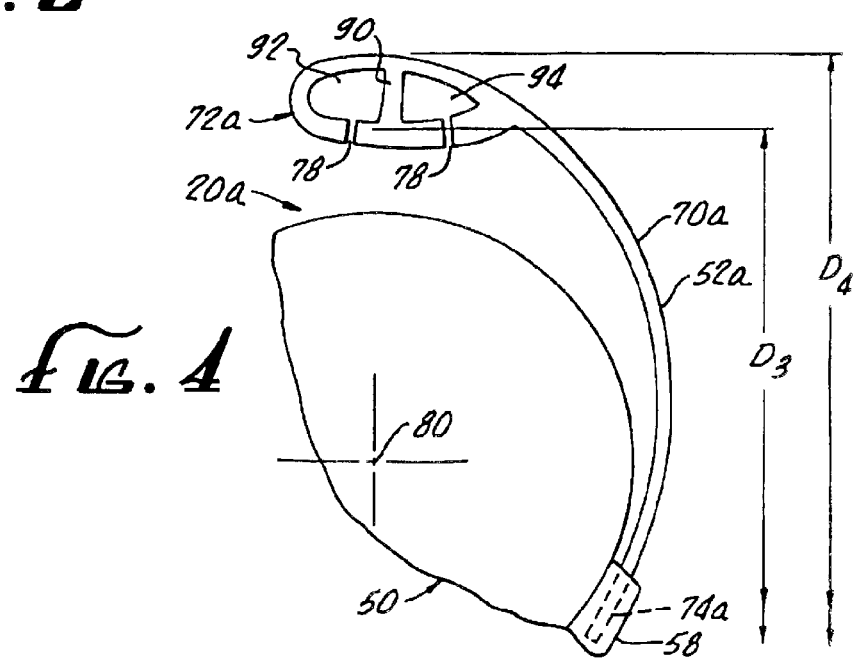

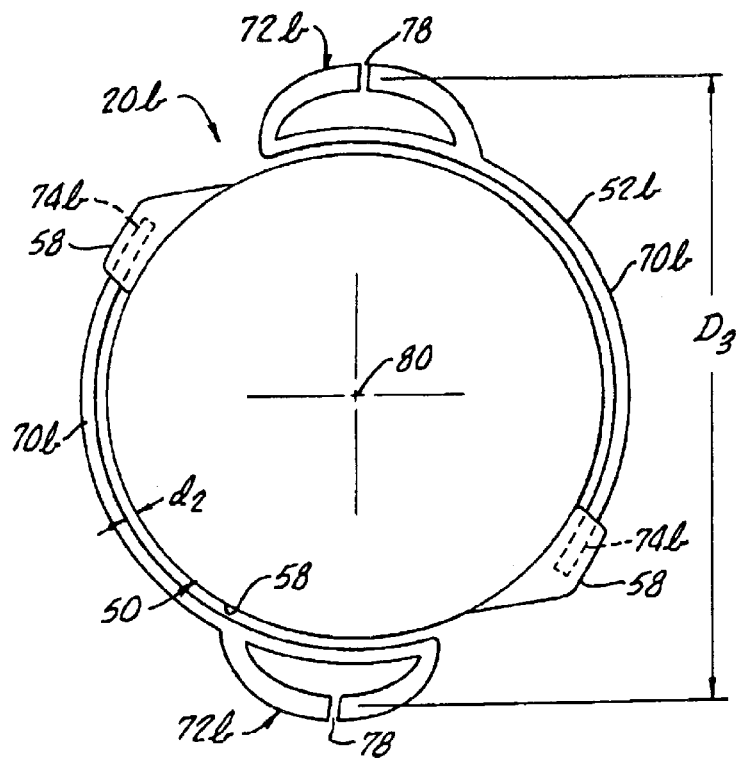
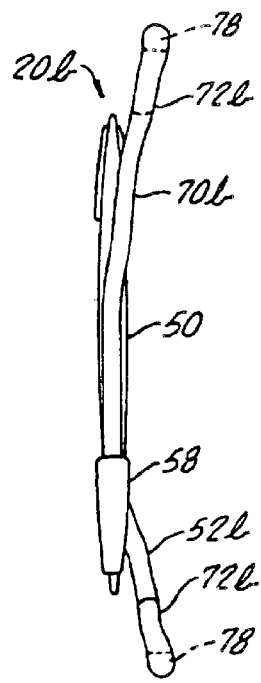
fig. 5
fig. 6
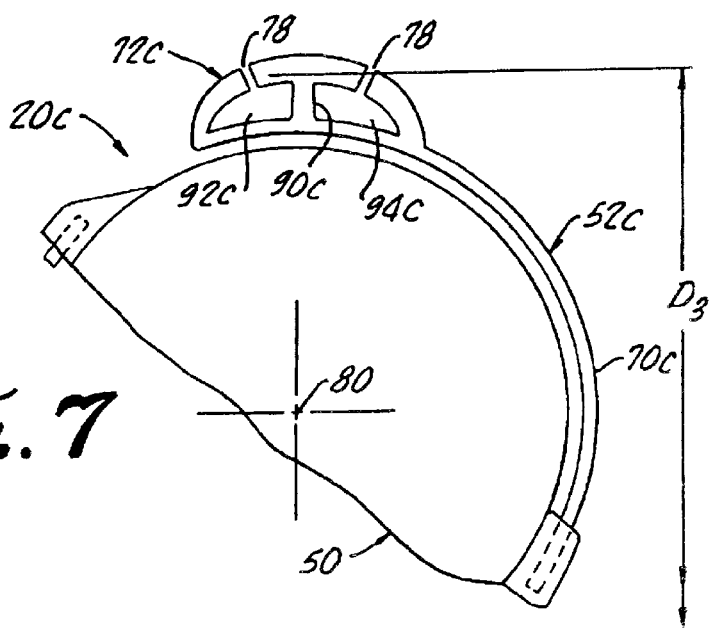
fig. 7

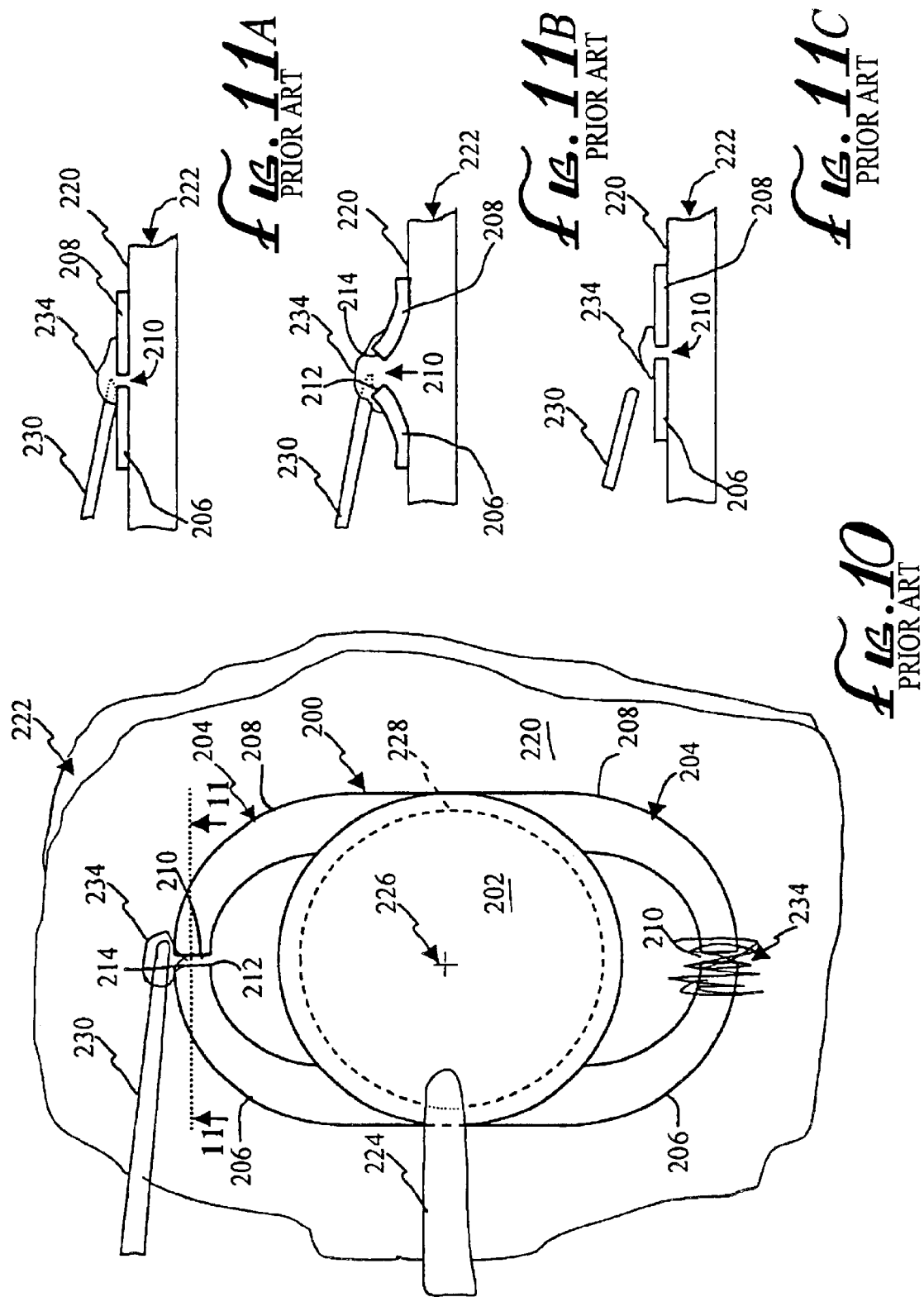

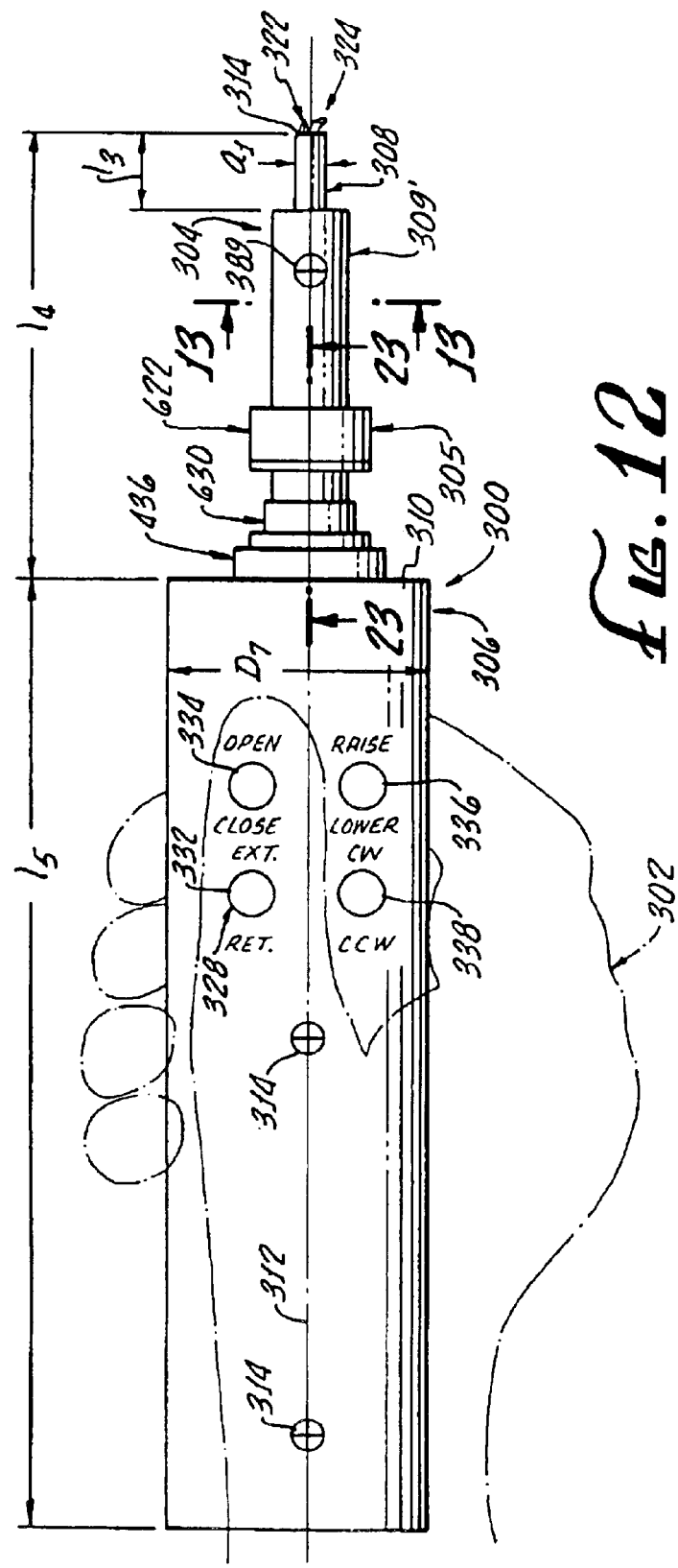

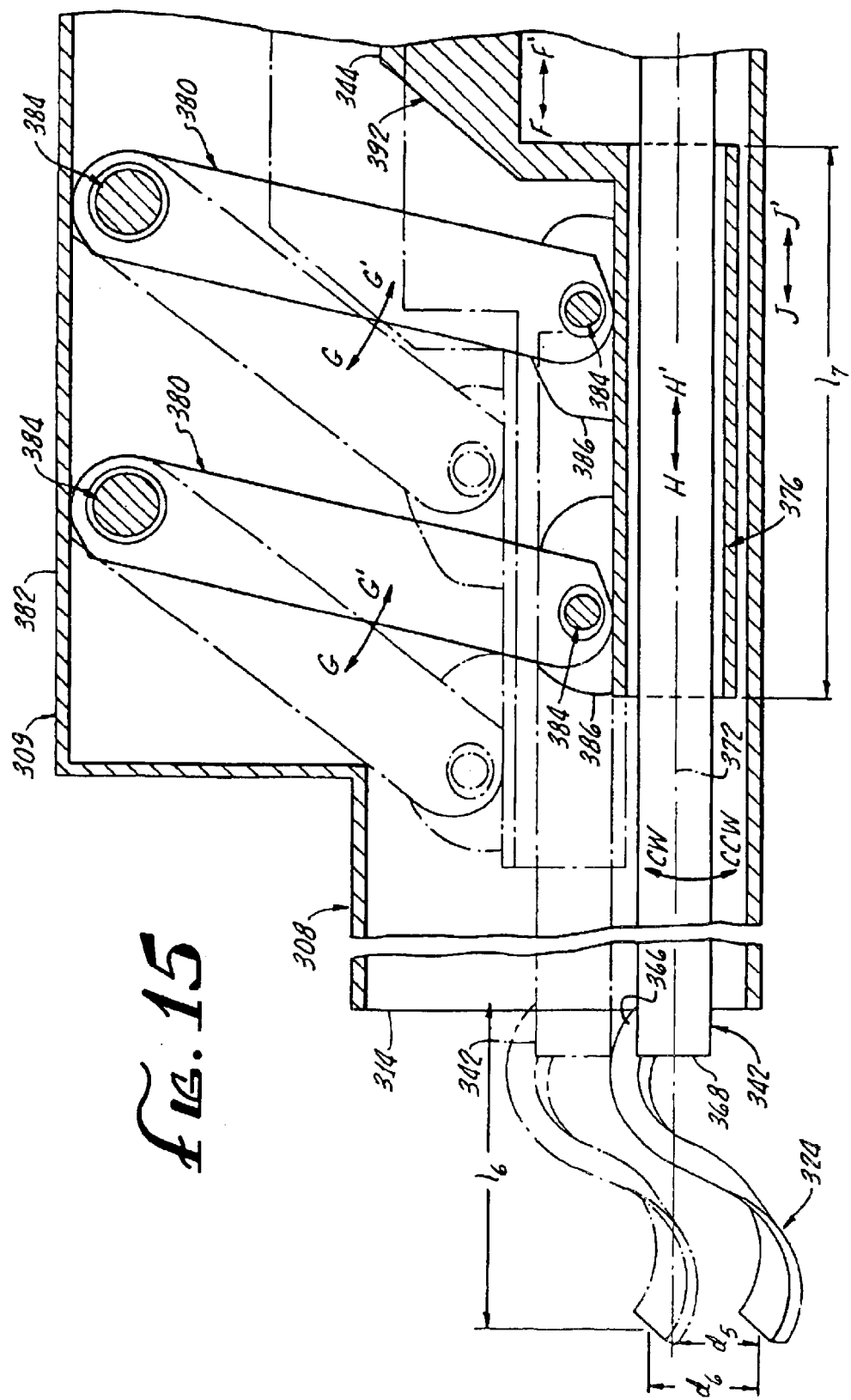

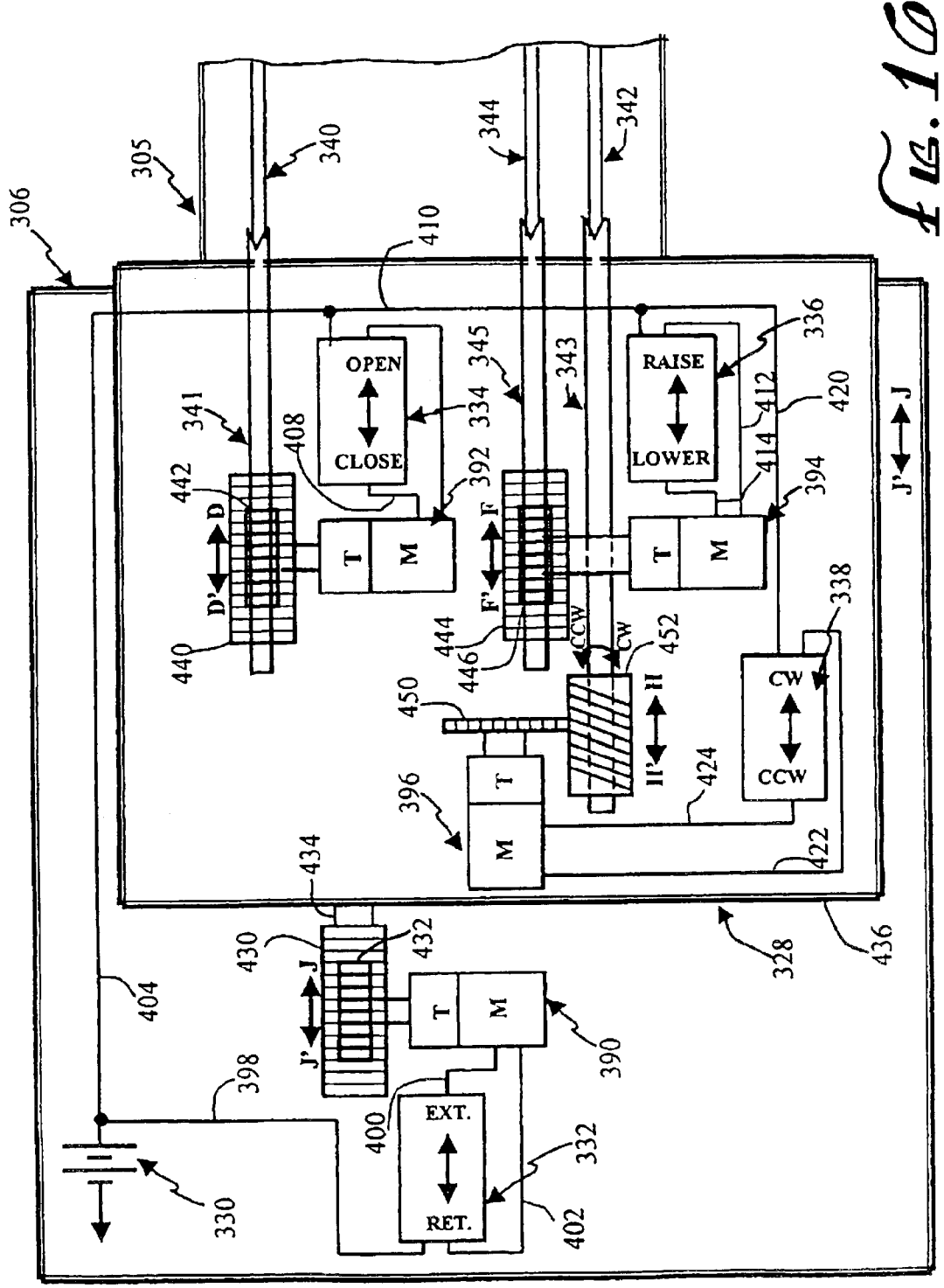

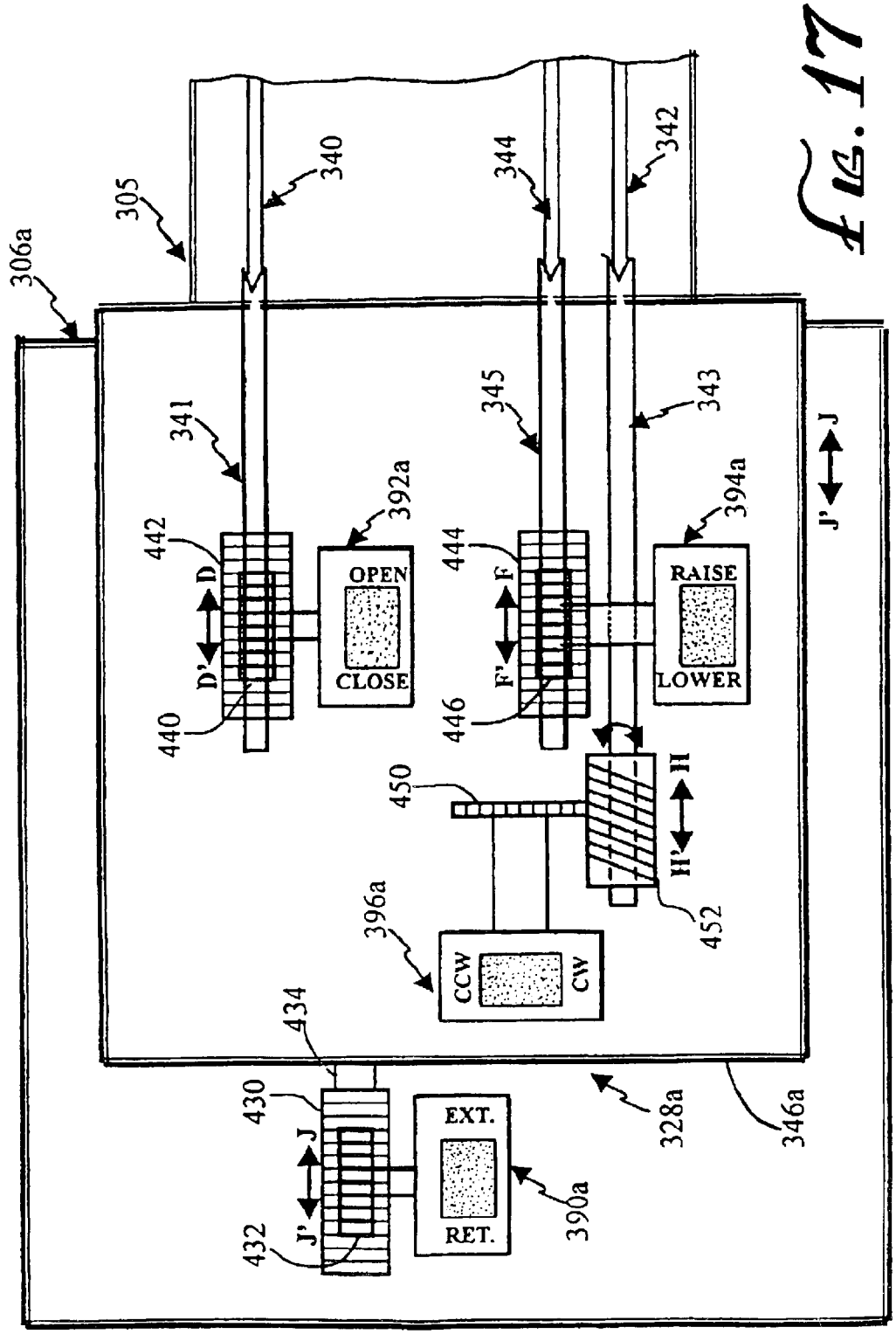

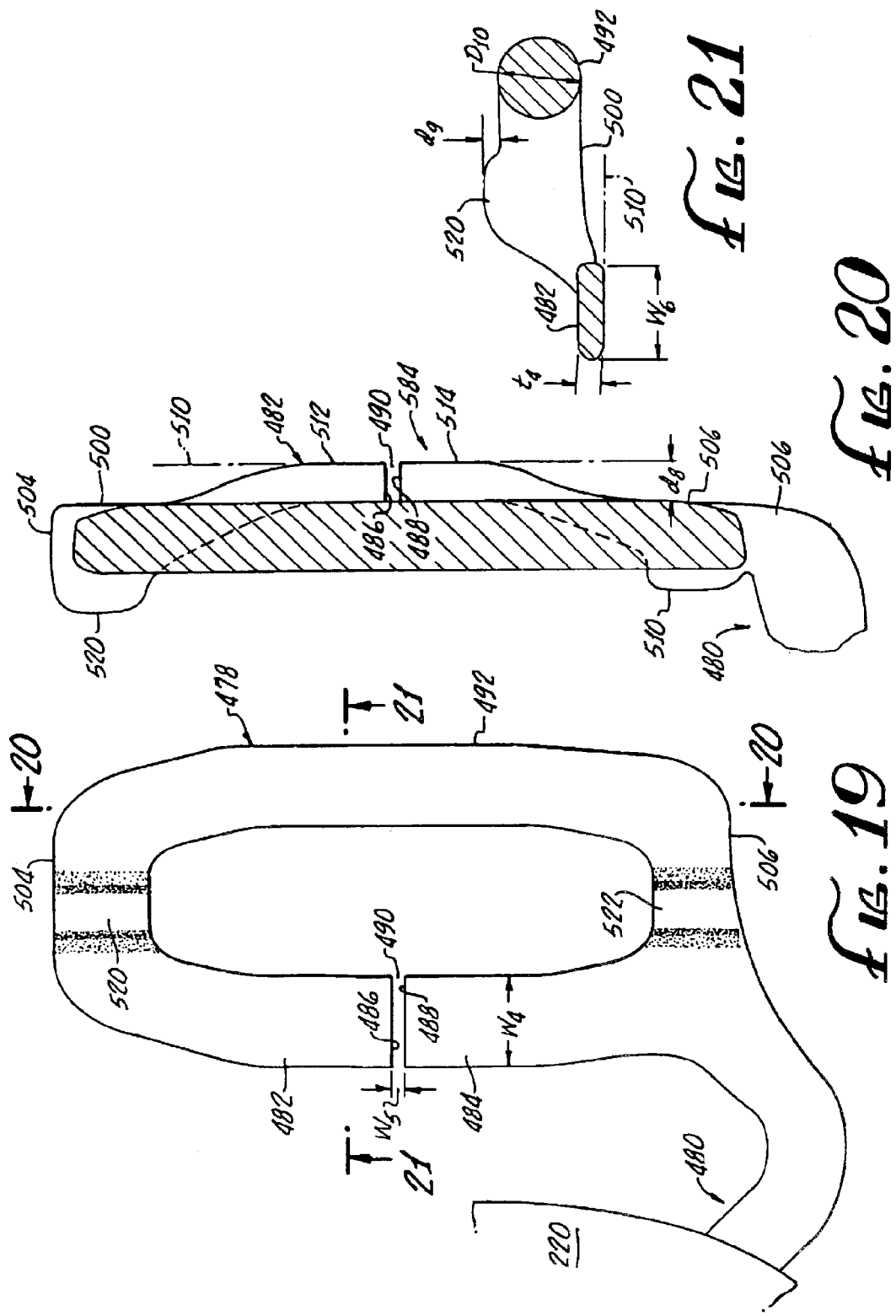

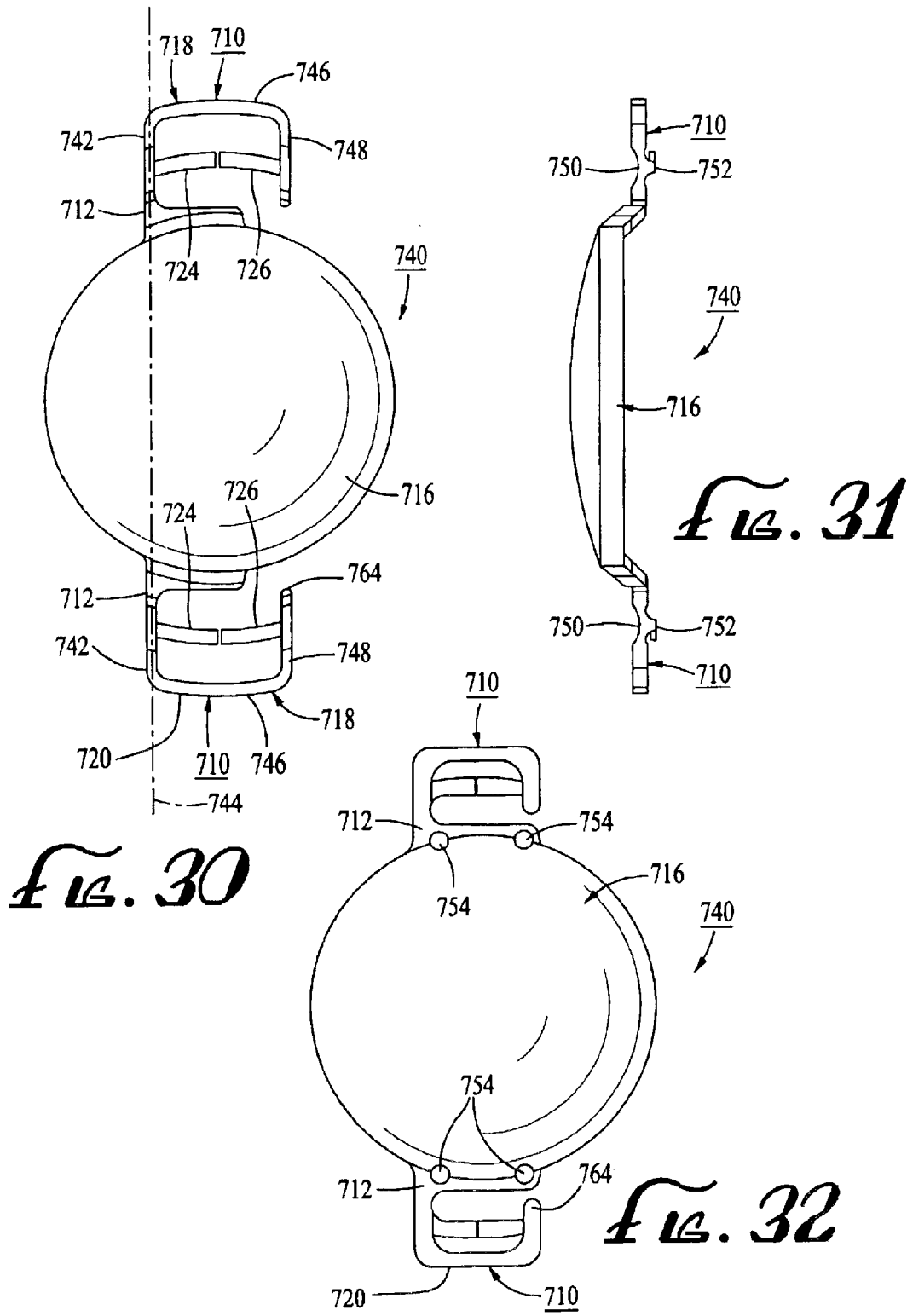

IRIS FIXATED INTRAOCULAR LENS SUITABLE FOR USE WITH ATTACHING INSTRUMENT

RELATED APPLICATIONS

This application is a continuation-in-part of U.S. patent application Ser. No. 09/489,069, filed Jan. 21, 2000 (now U.S. Pat. No. 6,342,058), which, in turn, was a continuation-in-part of U.S. patent application Ser. No. 09/312,566, filed May 14, 1999 (now U.S. Pat. No. 6,152,959).

FIELD OF THE INVENTION

The present invention relates generally to the field of ophthalmics, more particularly to ophthalmic devices, still more particularly to ophthalmic devices known as intraocular lenses (IOLs), and even more particularly to iris fixated intraocular lenses and to surgical instruments useful for attaching such lenses to an ocular iris.

BACKGROUND OF THE INVENTION

At the onset it may helpful to the understanding of the present invention to define the terms "phakic" and "aphakic" as related to human eyes. The term "phakic" is applied to an eye in which the natural ocular lens is still present. This is in contrast to an "aphakic" eye from which the natural ocular lens —or any reason—has been removed. A phakic eye is considered a dynamic or active eye because the living natural lens is subject to change over time, while an aphakic eye is considered a static eye.

One relatively common ocular problem is impaired or complete loss of vision due to the natural ocular lens becoming cloudy or opaque—a condition known as cataract. The formation of cataracts is typically associated with natural bodily aging, and most individuals over the age of about 60 years suffer from cataracts at least to some extent.

Cataracts cannot currently be cured, reversed, or even significantly arrested. Accordingly, the corrective action involves surgically removing the natural lens when the lens becomes so cloudy that vision is greatly impaired, the result being that a phakic eye becomes an aphakic eye.

After a defective natural lens has been surgically removed, the current vision-restoring practice (since about the 1940's) is to implant in the aphakic eye an artificial refractive lens called an intraocular lens (IOL) having an optic and optic fixation means. Previously, thick, heavy, high diopter spectacles were prescribed for aphakic eyes. Such spectacles however were and still are generally disliked by most patients for their weight and appearance.

Implantable IOLs were initially constructed from rigid polymethyl methacrylate (PMMA), a hard, biocompatable plastic material. More recently, IOLs have been constructed from a soft, elastically deformable, silicone or acrylic material that enables insertion of the IOLs through small ocular incisions.

In addition to the implanting of IOLs in aphakic eyes to restore vision after removal of the natural lens, considerable interest has recently arisen in implanting IOLs in phakic eyes to correct myopia, hyperopia, presbyopia or astigmatism problems associated with non-cataract natural lenses. This implanting of corrective IOLs in phakic eyes is an often-attractive alternative to the wearing of corrective spectacles or contact lenses, which limit certain activities and even certain professions, or having performed such surgical procedures on the cornea as radial keratomy (RK) or photo-radial keratectomy (PRK), which may not be desired by many individuals for various reasons. The implanting of refractive IOLs in phakic eyes to correct vision problems is considered to constitute one of the remaining frontiers of vision correction.

In an aphakic eye, a replacement IOL is now typically implanted in the posterior chamber of the eye from which the natural lens has been removed. In contrast, a corrective IOL for a phakic eye is most desirably implanted in the anterior chamber of the eye, forwardly of the intact natural lens remaining in the posterior chamber of the eye. (In some difficult cases, however, an IOL may be implanted in the anterior chamber after the natural lens has been removed from the posterior chamber.) The former type of IOL is called a posterior chamber IOL and the latter type is called an anterior chamber IOL. There are significant construction differences between these two types of IOLs.

With specific regard to anterior chamber IOLs (with which this application is concerned), there has been recently renewed interest in IOLs constructed for fixation to the iris for correcting vision in phakic eyes (although, some of the earliest IOLs for aphakic eyes were iris fixated anterior chamber IOLs). One reason for renewed interest in iris fixated IOLs for phakic eyes that fixating (i.e., attaching) the optic supporting structure directly to the iris itself avoids contact by the IOL with the sensitive filtration angle of the eye, thereby reducing subsequent ocular problems.

Iris fixated IOLs are disclosed in recent U.S. Pat. Nos. 4,215,440 and 5,192,319 to Jan Worst. Both of such patents disclose IOLs employing one or more optic fixation members formed having a pair of pincer arms which, by surgical manipulation when attaching the IOLs to an iris, pinch up and hold a small, anterior surface region of the iris in the narrow gap between the pincer arms. This pinching action detachably attaches the IOL to the iris so that the IOL optic is (ideally) fixated in the region of the iris opening (i.e., the pupil of the eye).

However, the present inventor considers that improvements to the iris fixated IOL designs disclosed in the two above-cited Worst patents are desirable. It is, therefore, a principal objective of the present invention to provide such improvements, particularly in the areas of improving optic centration and enabling small incision implanting of iris fixated IOLs.

Moreover, so far as is known to the present inventor, the attaching to the anterior surface of the iris of iris fixated IOLs of the type disclosed by the above-referenced Worst patents has involved a very tedious and difficult two-handed procedure requiring great skill, dexterity and training.

In this regard, a forceps is used by one of the IOL-implanting surgeon's hand to hold the IOL with the IOL optic centered on the iris. The surgeon uses his other hand to manipulate a needle (called an enclavation needle) to capture and lift a small region of iris stromal tissue adjacent the gap between the pair of pincer arms of one of the IOL fixation members (haptics).

This lifting of iris tissue in the gap region lifts opposing end regions of the pincer arms, thereby causing widening of the gap between the pincer arms. Thus, when the tip of the enclavation needle is withdrawn from the iris tissue, the lifted region of tissue becomes pinched in the narrowing gap between the pincer arms as the arms flex back downwardly to their normal position. This procedure results in the attachment of the related IOL fixation loop to the iris.

As a next step, the forceps and enclavation needle are switched between the surgeon's hands to perform the same attachment procedure for the second IOL fixation loop to the iris and the resulting attachment of the IOL to the iris.

This two-handed (i.e., bi-manual) IOL-to-iris fixation procedure is not only extremely difficult and very dependent upon the surgeon's skill, but it does not leave a free hand of the surgeon to perform other, ancillary procedures associated with the surgical implant of the iris fixated IOL.

In the parent application of the inventor, an iris fixated intraocular lens and an instrument for attaching same to an iris is described. The instrument is a combination enclavation needle and forceps instrument capable of one-handed use. In the implantation of an IOL, the forceps grips a portion of the haptic and the enclavation needle draws a small portion of the patient's eye material into a pincer gap disposed within the haptic. There is a problem, however, with respect to the instrument described in the inventor's parent application. That problem arises from the fact that the physical orientation of the enclavation needle and the forceps portions of the combination instrument is fixed with respect to each instrument. Either the enclavation needle is disposed above the forceps or the enclavation needle is disposed below the forceps instrument. It follows from this fact that a practitioner can only use a single combination instrument to fix that haptic of an IOL whose orientation corresponds to the orientation of the instrument. Since the practitioner must fix both haptics of the IOL by insertion of a combination instrument through a single incision in the eye of the patient, the practitioner can only attach a haptic of the IOL to the patient where the haptic has an orientation which corresponds to the orientation of the instrument. Thus, to attach a haptic to the IOL which has a reverse orientation, the practitioner must use a combination instrument having such reverse configuration. This means that a practitioner is required to purchase and maintain two separate combination instruments each having opposite orientations of enclavation needle and forceps. This presents a significant cost disadvantage to the practitioner.

Accordingly, there is a need for an intraocular lens capable of being installed by a single combination enclavation needle and forceps instrument.

BRIEF DESCRIPTION OF THE DRAWINGS

The present invention can be more readily understood by a consideration of the following detailed description when taken in conjunction with the accompanying drawings, in which:

FIG. 2 is a front view of one embodiment of a three piece iris fixated IOL having features of the present invention, showing the optic and an opposing pair of optic support or fixation members (haptics), each terminating in an elongated fixation loop having a narrow pincer gap for enabling detachable attachment of the IOL to the anterior surface of a patient's iris, the pincer gaps being shown directly facing the optic;

FIG. 3 is a side view of the IOL of FIG. 2, showing forward vaulting of the optic relative to the fixation loops;

FIG. 4 is a partial front view of a variation fixation loop corresponding to the fixation loops shown in FIG. 2, showing a spaced apart pair of iris pincer gaps defined in the elongated vertically-divided fixation loop, both of such gaps shown directly facing the optic;

FIG. 5 is a front view of a variation three piece iris fixated IOL having features of the present invention, showing the optic and an opposing pair of haptics, each such haptic shown curving closely around the optic and terminating in an elongated fixation loop having a narrow, perpendicular pincer gap for enabling detachable attachment of the IOL to a patient's iris, the pincer gaps being shown facing away from the optic;

FIG. 6 is a side view of the IOL of FIG. 5, showing forward vaulting of the optic relative to the fixation loops;

FIG. 7 is a partial front view of a variation fixation loop corresponding to the fixation loops shown in FIG. 5, showing a spaced apart pair of iris pincer gaps defined in the elongated vertically-divided fixation loop, both of such gaps shown directed away from the optic;

FIG. 10 is a plan view of a prior art iris fixated IOL illustrating the previously-used, two-handed iris attachment process involving the use by one hand (not shown) of forceps to hold the IOL in position against the anterior surface of the iris and simultaneously, involving the use by the other hand (also not shown), to manipulate a separate enclavation needle to engage (i.e.,pierce), with the needle tip, the anterior surface of the iris adjacent the upper pair of IOL fixation loop pincer arms and lift a small region of the iris tissue into the gap between the pincer arms;

FIG. 11 is a series of cross sectional views taken along line 11—11 of FIG. 10; FIG. 11A showing a small region of iris issue adjacent the pincer arm gap engaged and lifted by the tip of the enclavation needle; FIG. 11D showing the ends of the pincer arms adjacent the pincer arm gap, with opposing end regions of the pincer arms shown flexed upwardly and spread apart by the lifted tissue; and FIG. 11C showing the enclavation needle withdrawn from the iris tissue and opposing end regions of the pincer arms flexed back into their iris-attachment position, with a small region of iris tissue pinched in the pincer arm gap to thereby attach the pincer arms—and the associated IOL—to the iris;

FIG. 12 is a perspective drawing of a combination forceps and enclavation needle instrument having features of the present invention useful for attaching an iris fixated IOL to the anterior surface of a patient's iris, showing a forceps tip and needle tip projecting from a slender operating head portion of the instrument and showing external elements in a handle portion of the instrument for enabling the manipulation of the forceps and needle tips by one hand of a user;

FIG. 15 is a longitudinal cross sectional drawing looking along line 15—15 of FIG. 13, illustrating details of the enclavation needle tip portion of the cowbination instrument depicted in FIG. 12, showing in solid lines an exemplary spiral enclavation needle tip in its lowered position, showing in phantom lines the needle tip in its raised position, and further showing the mechanism by which the needle is raised and lowered;

FIG. 16 is a schematic drawing showing electrical implementation of the operating and control system of the combination forceps and enclavation needle instrument depicted in FIG. 12, showing four rotational or advancing/retracting miniature, reversing electrical motors and associated gears, and showing associated electrical switches for selective operation of the motors;

FIG. 17 is a schematic drawing of a variation operation and control system that is the mechanical equivalent of the electrical operating and control system depicted in FIG. 16, four thumb-wheels being shown substituted for the four reversible motors and associated electrical switches;

FIG. 18 is a series of enlarged drawings showing several different shapes of enclavation needle tips.

FIG. 19 is a greatly enlarged plan view of a modified haptic fixation loop of the iris fixated IOL similar to that depicted in FIG. 2, the fixation loop being configured to facilitate operation of the combination forceps and enclavation needle instrument, the fixation loop having thickened end regions for rigidity;

FIG. 20 is a cross sectional view taken along line 20—20 of FIG. 19, showing end regions of the fixation loop raised relative to central regions of the loop;

FIG. 21 is a cross sectional view taken along line 21—21 of FIG. 19, showing a representative one of thickened end regions of the fixation loop;

FIG. 22 is a series of drawings depicting, by way of specific example, operation of the combination forceps and enclavation needle instrument having features of the present invention in connection with the haptic fixation loop depicted in FIGS. 19–21; with the helical needle tip depicted in FIG. 18A and with the insertion portion of the instrument positioned at a right angle relative to a long axis of the fixation loop.

FIG. 30 is a plan view of an intraocular lens having features of the invention;

FIG. 31 is a side view of the intraocular lens illustrated in FIG. 30;

FIG. 32 is a plan view of another embodiment of an intraocular lens having features of the invention;

In the various FIGS., the same elements and features are given the same reference numbers. In the various variation variations, corresponding elements and features are given the same reference numbers as first set forth, followed by an "a", "b", "c", and so on, as appropriate and/or as will be evident in the following DESCRIPTION.

DETAILED DESCRIPTION

The following discussion describes in detail one embodiment of the invention and several variations of that embodiment. This discussion should not be construed, however, as limiting the invention to those particular embodiments. Practitioners skilled in the art will recognize numerous other embodiments as well.

The invention claimed herein is the intraocular lens illustrated in FIGS. 19 and 27–36. For a proper understanding of the invention, however, the intraocular lenses and the combination enclavation needle and forceps instrument described in the inventor's parent application are described immediately hereafter.

Figure 1:
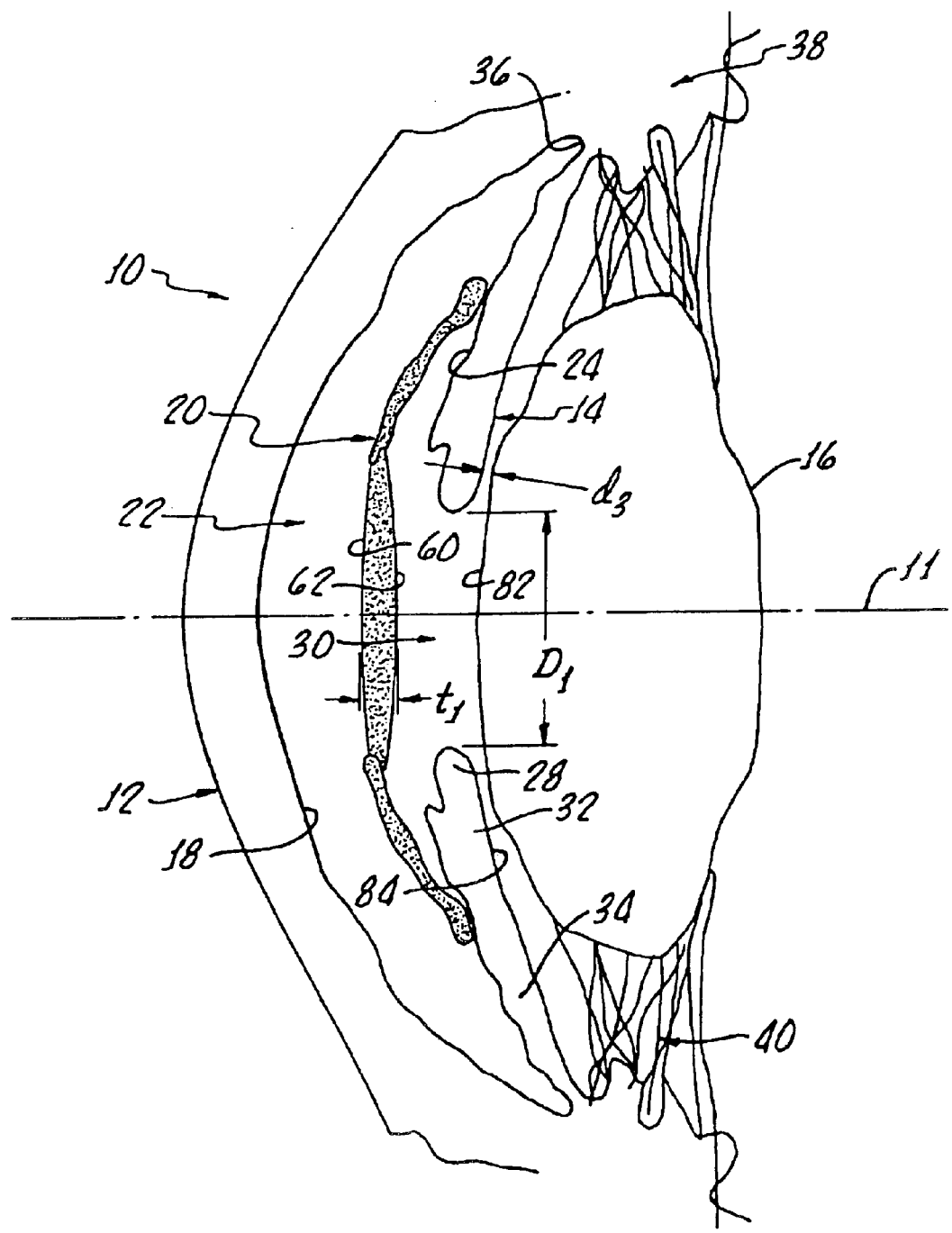
FIG. 1 is a vertical cross sectional drawing of forward regions of a representative human eye, showing the cornea, iris and natural lens and showing an iris fixated intraocular lens (IOL) having features of the present invention implanted in the anterior chamber of the eye and fixed to the anterior surface of the iris.

Background Information Regarding the Disclosure in the Applicant's Parent Application There is shown in FIG. 1, in vertical cross section, a forward region 10 of a representative human eye having an optical axis 11 (Axis of symmetry). Depicted in the FIG. are a cornea 12, an iris 14 and an intact, natural crystalline lens 16. A (posterior) corneal endothelium surface 18 is identified on cornea 12.

An iris fixated intraocular lens (IOL) 20 is shown implanted in an anterior chamber 22 of eye region 10 (posterior to corneal endothelium surface 18) and fixated, in a manner described below, to an anterior surface 24 of iris 14.

Identified in FIG. 1, to facilitate the understanding of the present invention, is an annular pupiliary spincter region 28 of iris 14 that surrounds and controls a pupil or pupiliary opening 30 having a diameter, $D_1$, that typically is no greater than about 8 mm for normal vision.

Further identified are an annular iris collarette region 32 and an annular pupiliary dilator muscle region 34 of iris 14. An annular chamber angle 36 is identified at a peripheral edge region of iris 14, as is an annular trabecular meshwork 38. An annular ciliary process 40 is indicated at the peripheral attachment of natural lens 16.

As is further depicted in FIG. 1, iris fixated IOL 20 is fixated to iris anterior surface 24 in the general region of iris collarette 32 (the thickest region of iris 14), radially outwardly from pupiliary sphincter 28.

Shown in FIGS. 2 and 3, comprising iris fixated IOL 20 are an optic 50 and a pair of opposing, similar and preferably identical, fixation members or haptics 52. Projecting sidewardly (radially) from opposite sides of a peripheral edge 56 of optic 50, and preferably formed in one piece with the optic, are similar structural haptic attachment abutments or bosses 58. Optic 50, which has respective anterior and posterior surfaces 60 and 62 (FIGS. 1 and 3), may be constructed as convex-convex (as depicted in FIG. 1), convex-concave, convex-planar, or concave-planar or concave-concave, all such and other configurations being within the scope of the present invention. Optic 50 may advantageously be provided in the diopter range between about −15 and about +15.

It is preferred that optic 50 be constructed from an elastically deformable material, such as a silicone or acrylic material, enabling the optic to be folded, rolled or otherwise deformed so that IOL 20 can be implanted through an ocular incision no larger than about 3.5 mm. It is therefore preferable that the material from which optic 50 is constructed have an index of refraction of at least about 1.46 and that the optic have a diameter, $D_2$, of between about 5.5 mm and about 7.0 mm (FIG. 3) and a center thickness, $t_1$, no greater than about 0.8 mm (FIG. 1).

Each of haptics 52, which are preferably constructed (as by micro-machining) from polymethyl methacrylate (PMMA), is formed having an arcuate, flexible proximal end region 70 and a generally flat, loop-shaped distal end region 72. A proximal end 74 of each haptic 52 is fixed into an associated one of bosses 58 (FIG. 2) so that haptic proximal end region 70 extends in a direction tangential to optic edge 56. Such haptic-to-optic fixation can be of any type used by IOL manufacturers for the secure attachment of haptics to soft, flexible optics.

Haptic proximal end region 70 is arcuate in plan view and arches away from optic 50 (FIG. 2). Further, proximal end region 70 is made flexible, particularly in a plane parallel to the plane of optic 50, by preferably having a width, $w_1$, of about 0.25 mm and a thickness, $t_2$ (FIG. 3) of about 0.35 mm. Preferably portions of haptic 52 defining distal end region loop 72 have about the same thickness as set forth for haptic proximal end region 70, and may be somewhat wider, as set forth below.

The loop into which haptic distal end region 72 is formed may be of a variety of shapes. However, the end region loop is shown in FIG. 2 as being elongated into a curved shape having a length, $l_1$ and flattened into a width, $w_2$. By way of example, with no limitation intended or implied, such loop length, $l_1$, may be about 3.0 mm and such loop width, $w_2$, may be about 1.0 mm.

A side region 76 of distal end region loop 72 that is closest to and directly faces optic 50 is formed defining an iris pincer gap 78 (FIG. 2) having a width, $w_3$, of about 0.1 mm and a length, $l_2$, of about 0.4 mm. Iris pincer gap 78 is shown oriented in a radial direction relative to a center 80 of optic 50, but may alternatively be oriented in another direction. As further, shown in FIG. 2, both iris pincer gaps 78 of the two haptics 52 are centered on a diameter, $D_3$, which is preferably about 8.5 mm. Pincer gaps 78 of both haptics 52 also lie generally on a common plane 82 (FIG. 3), the haptics being arched so that optic 50 is vaulted forwardly into anterior chamber 22 (FIG. 1) with posterior surface 62 anterior of plane 82 by a distance, $d_1$, that is preferably about 0.5 mm.

Overall diameter, of IOL 20 (to ends of haptics 52) is preferably between about 7.5 mm and about 10 mm so that the IOL haptics engage iris 14 at iris collarette region 32, as noted above (FIG. 1).

As a result of the flexibility of haptics 52, after one haptic has been attached to iris 14 by a pinching action (more particularly described below), optic center 80 can be easily aligned with optical axis 11 by flexing of the second haptic 52 before the second haptic is attached to the iris. Thus, centration of optic 50 on optical axis 11 of the eye is easily achieved.

Moreover, with optic 50 constructed from an elastically deformable material, IOL 20 can be implanted through a small ocular incision, as is important to minimize surgical trauma and possible complications, and reduce patient recovery time, all as compared to the surgical procedure required to implant a rigid iris fixation IOL. Further in this regard, the explanting of the flexible IOL 20, in the event explanting becomes necessary as the patient's vision changes with time, is also made easier.

From the foregoing, it will be appreciated that many variations to IOL 20 and particularly to haptics 52 which attach the IOL to iris 14 are possible and are to be considered as being covered by the present invention.

One such variation is shown in FIG. 4 in connection with a variation IOL 20a, which is identical for descriptive purposes to above-described IOL 20 except as otherwise particularly described below. Corresponding elements and features are given the same reference numbers set forth above followed by an "a".

As shown, a looped distal end region 72a of a haptic 52a (corresponding to haptic 52) is divided radially (relative to center 80 of optic 50) by a narrow wall 90 into respective first and second loop sectors 92 and 94. Each such sector 92 and 94 is constructed to define an iris pincer gap 78 directly facing optic 50. Thus, each haptic 52a (only a representative one of which is shown) incorporates in distal end region 72a a spaced-apart pair of iris pincer gaps 78. This described doubling of the number of iris pincer gaps 78 in haptic loops 72a may sometimes be advantageous in securely detachably fixing IOL 20a to iris 14.

Another such variation is shown in FIGS. 5 and 6 in connection with a variation iris fixation IOL 20b, which is identical for descriptive purposes to above-described IOL 20 except as otherwise particularly described below. Corresponding elements and features are given the same reference numbers set forth above followed by a "b".

A principal distinction between IOL 20b and above-described IOL 20 relates to pincer gaps 78 on haptic loops 72b facing away from optic 50 instead of directly facing the optic in the case of above-described IOL 20. Because pincer gaps 78 are spaced apart the same distance, $D_3$ (before disclosed in connection with IOL 20), proximal regions 70b of haptics 52b curve more closely around optic 50. Haptics 52b, are generally spaced from optic edge 56 a distance, $d_2$, that is at least about equal to a closest separation distance, $d_3$ (FIG. 1), between anterior surface 82 of natural lens 16 and posterior surface 84 of iris 14 (a distance typically of about 0.3 mm).

Since haptics 52b are otherwise similar to above-described haptics 52, this increased C-curvature of haptics 52b may provide somewhat increased haptic flexibility. Moreover, orienting pincer gaps 78 on haptic loops 72b away from optic 50 may, in some instances, facilitate fixation of the IOL to iris 14. The vaulting of optic 50 relative to haptic loops 72b is preferably the same as disclosed above relative to IOL 20.

FIG. 7 depicts another variation iris fixated IOL 20c, which is identical for descriptive purposes to above-described IOL 20b except as otherwise particularly described below. Previously described features and elements are given the same reference number followed by a "c".

As can be seen, IOL 20c combines the described double pincer gap features shown for IOL 20a in FIG. 4 with IOL 20b (FIGS. 5 and 6.). Thus, as shown in FIG. 7, representative haptic loop 72c is vertically divided by a narrow wall 90c into first and second loop sectors 92c and 94c, respectively. Each sector 92c and 94c has defined a pincer gap 78 that faces away from associated optic 50.

Pincer gaps 78 on both haptic loops 72c (only one such loop being shown) are spaced a distance $D_3$ (defined above) apart.

Figure 8:
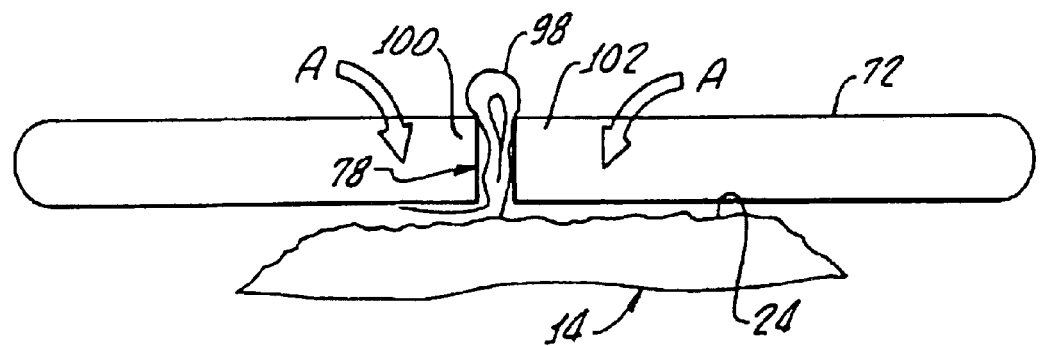
FIG. 8 is a drawing depicting the manner in which a representative right angle pincer gap, such as those shown in FIGS. 2, 4, 5 and 7, is operative for pinching an anterior surface region of an iris in a manner detachably attaching the associated fixation loop and thus the associated IOL to the iris.

FIG. 8 depicts the manner in which a representative one of pincer gaps 78, on a representative haptic distal end region loop 72 pinches up a small surface segment 98 of iris tissue into the gap, thereby releasably or detachably fixing the associated haptic (e.g., haptic 52), and hence the associated IOL (e.g., IOL 20), to iris 14.

This pinching up of iris segment 98 is accomplished, for example, by deflecting haptic loop regions 100 and 102 on each side of gap 78, downwardly (direction of Arrows "A") into iris surface 24. When the loop regions are released, they return to their original shape, thereby trapping iris segment 98 in gap 78.

It is to be understood that variations of the iris pincer gap may be made within the scope of the present invention and used in place of above-described pincer gap(s) 78. An example of such a variation is depicted in FIG. 9, in which a slanted iris pincer gap 78d (corresponding to above-described pincer gap 78) is depicted formed or defined in a representative haptic distal end region loop 72d (corresponding to above-described distal end region loop 72).

Figure 9:
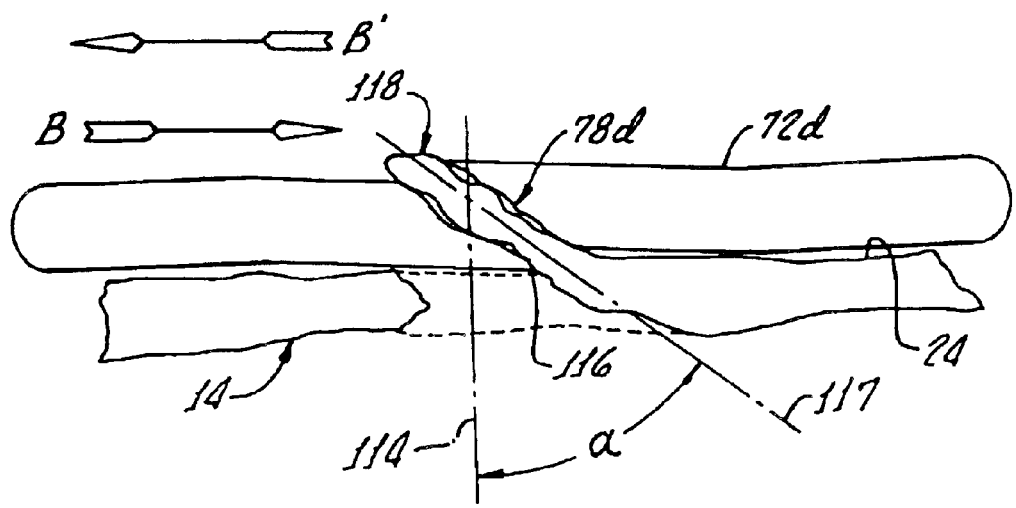
FIG. 9 is a drawing depicting the manner in which a representative angled pincer gap, corresponding to the right angle pincer gaps shown in FIGS. 2, 4, 5 and 7 is used to engage the anterior surface of an iris in a manner detachably attaching the associated fixation loop and thus the associated IOL to the iris.

Pincer gap 78d is depicted in FIG. 9 as formed or defined along a line 112 that is at an angle, $\alpha$, relative to a line 114 perpendicular to end region loop 72d. Preferably, slant angle, $\alpha$, is between about 30 degrees and about 60 degrees, with a slant angle of about 45 degrees being most preferred.

It is evident from FIG. 9 that when end region loop 72d is pressed against iris anterior surface 24 and is pushed or advanced in the direction indicated by Arrow "B", a sharp, leading lower edge 116 at gap 78d cuts into iris 14. This causes a small sliver 118 of iris 14 to be extruded into gap 78d, to thereby detachably fixate end region loop 72d, and hence associated haptic and IOL (neither shown in FIG. 9) to iris 14.

Distal end region loop 72d can be detached from iris by merely rotating the end region loop back in the direction indicated by Arrow "B'".

There is depicted in FIG. 10, by way of example and for comparative purposes, an iris fixated IOL 200 of the general configuration disclosed in the above cited Worst patents.

Shown comprising IOL 200 are an optic 202 and an opposing pair (i.e., upper and lower, as depicted) of IOL fixation loops or members or haptics 204. Each fixation loop 204 comprises respective first and second pincer arms 206 and 208 that define a pincer gap 210 between opposing pincer arm end surfaces 212 and 214, respectively.

FIG. 10 further illustrates the heretofore-used (so far as is known to the present inventor) most commonly used procedure for attaching IOL 200 to an anterior surface 220 of iris 222, as has been briefly described in the foregoing BACKGROUND OF THE INVENTION.

As depicted, forceps, only a tip 224 of which is shown, are used by one hand (not shown) of the IOL-implanting surgeon to grip an edge region of IOL optic 202. Forceps tip 224 hold IOL optic 202 in a manner holding IOL 200 against iris anterior surface 220 with optical axis 226 of the IOL optic aligned with the optical axis of pupil 228 (i.e., the optical axis of the eye).

With IOL 200 held and positioned in the above-described manner by forceps tip 224, an enclavation needle, only a tip region 230 of which is shown, is manipulated by the implanting surgeon's other hand (not shown) so that the needle tip pierces iris anterior surface 220 adjacent pincer gap 210 of one of the fixation loops 204—the uppermost fixation loop being depicted.

The needle is then manipulated so that needle tip portion 230 engages and starts lifting a small region 234 of iris stromal tissue, as also depicted in FIG. 11A.

As depicted in FIG. 11B, with forceps tip 224 still holding IOL 200 properly positioned against iris anterior surface 220, needle tip portion 230 is then raised in a manner lifting engaged iris tissue region 234 into pincer gap 210. This tissue region 234 lifting process flexes end regions of pincer arms 206 and 208 upwardly, thereby widening pincer gap 210.

Finally, as depicted in FIG. 11C, needle tip 230 is withdrawn from iris tissue region 234. Pincer arms 206 and 208 then flex back downwardly to their unflexed position (Ref. FIG. 11A), closing gap 210 and pinching iris tissue region 234 in the gap (as is also depicted for the lowermost fixation loop 204 of IOL 200 in FIG. 10).

Alternatively (not depicted), needle tip portion 230 may be used to depress an open end region of one of pincer arms 206 or 208 into iris anterior surface 220 such that when the pincer arm end region is released by needle tip region 230, some iris stromal tissue, corresponding to tissue region 234 is pinched in pincer arm gap 210.

The above-described iris tissue pinching in pincer gaps 210 of both fixation loops 204, detachably attaches IOL 200 to iris anterior surface 220. If detachment of IOL 200 from iris surface 220 later becomes necessary for any reason, the procedure described above is essentially reversed.

Although the above-described procedure for fixating IOL 200 to iris anterior surface 220 may appear relatively simple, in actual practice the procedure is one of the most difficult or all surgical procedures. This is because the procedure requires unusually great manual dexterity of both hands simultaneously.

In order to reduce the currently great difficulty in performing the foregoing iris fixation surgical procedure and improve reproducibility of the fixation procedure, the present inventor has invented a combination forceps and enclavation needle instrument 300 (FIG. 12) that can be easily operated by one hand 302 as more particularly described below.

As shown, instrument 300 comprises an elongate operating head portion 304, an intermediate, operating head separation portion or means 305 and an elongate, preferably cylindrical, handle or barrel portion 306. operating head portion 304 includes a tubular, ocular insertion member 308 which, with separation portion or means 305, extends from a distal end 310 of handle or barrel portion 306 along a longitudinal axis 312 of the instrument.

Handle portion 306 may advantageously be constructed of two longitudinal half sections (not individually shown) attached together by two screws 314 to enable internal access for assembly, maintenance and any required repair.

Projecting from an open, distal end 314 of operating head portion 304 are a forceps tip 322 and an enclavation needle tip 324, also as more particularly described below.

With no limitations being intended or implied, a tubular insertion member 308 of operating head portion 304 may have a length, $l_3$, of about 8 mm. Insertion member 308 is preferably elliptical or oval in transverse cross section, having a major cross sectional dimension, $a_1$, of no more than about 2.5 mm and a minor cross sectional dimension, $a_2$, of no more than about 1.9 mm (see FIG. 13) to enable its insertion through a small ocular incision. An overall length, $l_4$, of operating head portion 304 may be about 40 mm.

Without limitation, handle portion 306 may have a length, $l_5$, of about 170 mm, and is preferably round with an outside diameter, $D_7$, of about 25 mm.

Installed in handle portion 306 are needle and forceps tip operating and control system or means 328 which is preferably electrical powered, as more particularly described below. System 328 is configured for enabling forceps tip 322 and enclavation needle tip 324 to be operated by one user hand 302 to detachably attach (and/or remove) an iris fixated IOL, similar to IOL 20 (FIG. 2) in a manner similar to that described above for IOL 200 (FIGS. 10–11).

Also shown in FIG. 12 comprising externally accessible portions of operating and control system 328 are respective first, second, third and fourth momentary-on/off/momentary-on electrical switches 332, 334, 336 and 338 by which forceps tip 322 and needle tip 324 can be micro-manipulated by the user's one hand 302.

As more particularly described below, first switch 332 is electrically connected for selectively moving both forceps tip 322 and needle tip portion 324 in extended and retracted axial directions a limited adjustment distance of several mm. Second switch 334 is electrically connected for selectively opening and closing forceps tip 322. Third switch 336 is electrically connected for selectively raising and lowering needle tip 324. Fourth switch 338 is electrically connected for simultaneously partially rotating needle tip 324 in clockwise (CW) and counterclockwise (CCW) directions with associated extending and retracting of the needle tip for helical needle tips, as described below.

Figure 13:
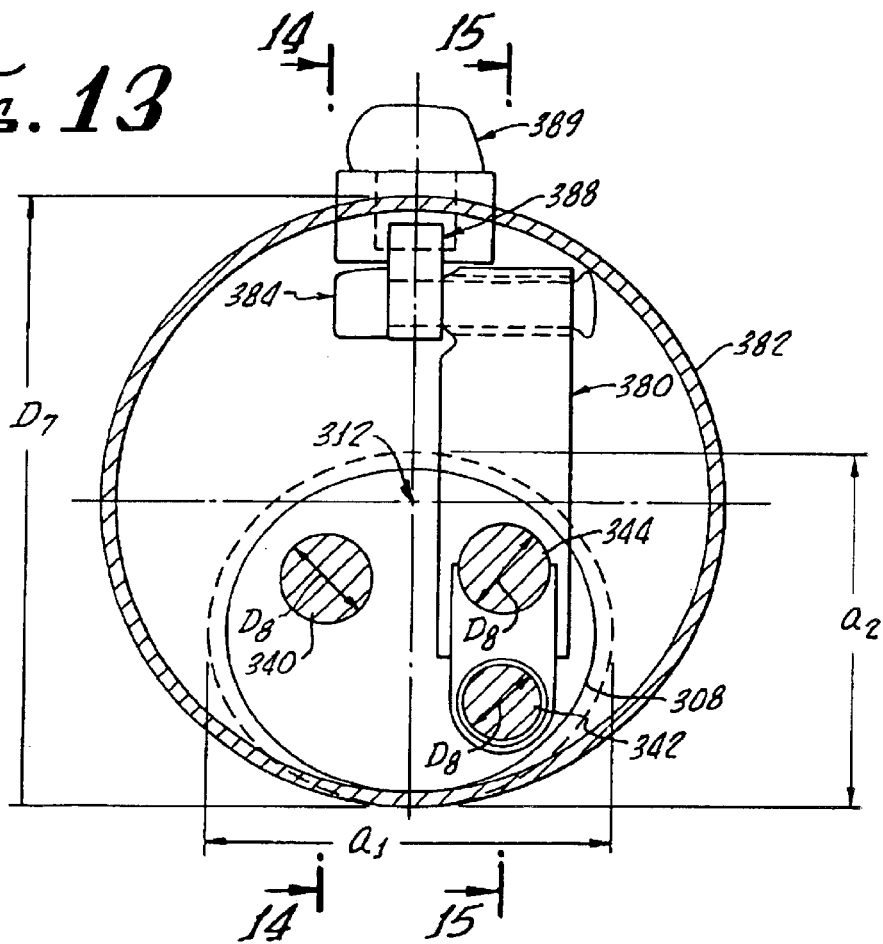
FIG. 13 is a transverse cross sectional drawing looking along line 13—13 of FIG. 12, showing three operating rods of a forceps tip and needle tip operating and control system.

FIG. 13 is a transverse cross sectional drawing of insertion member 308 showing a rod or pin 340 for operating forceps tip 322 and rods or pins 342 and 344 for operating needle tip 324. Rods or pins 340, 342 and 344 preferably each have a cross sectional diameter, $D_8$, which is about 0.5 mm.

Figure 14:
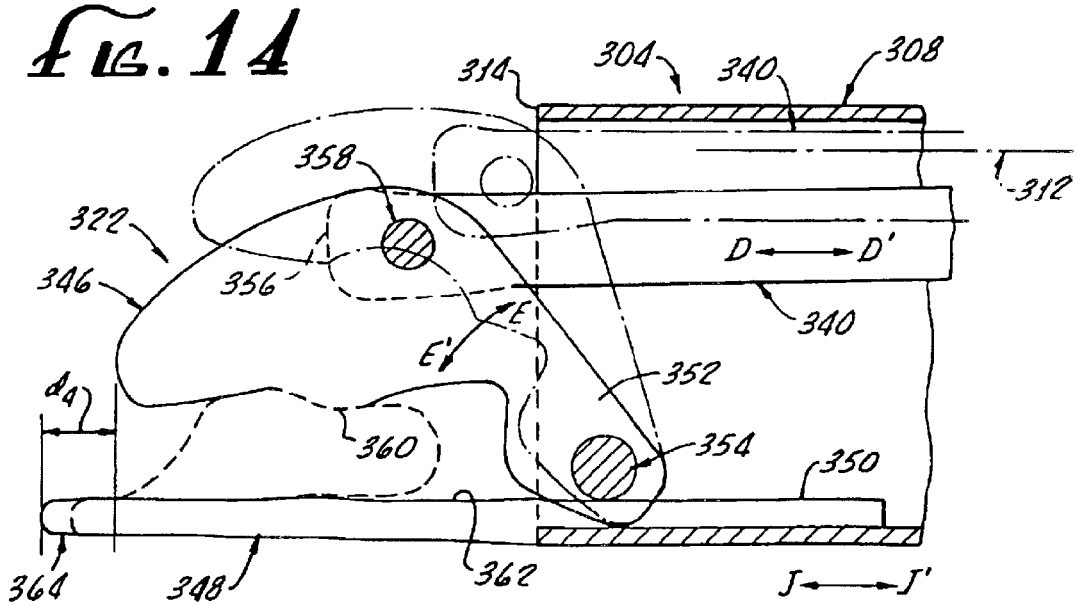
FIG. 14 is a longitudinal cross sectional drawing looking along line 14—14 of FIG. 13, showing details of the forceps tip portion of the combination instrument depicted in FIG. 12, showing upper and lower jaws of the forceps tip in both the closed and open positions, the closed position showing the forceps tip (in solid lines) gripping a portion of the IOL fixation loop (shown in broken lines) and the open forceps tip position being shown dotted lines, and further showing pivotal mounting of a lower region of the upper jaw to the instrument tip and showing an operating pin pivotally attached to a mid region of the upper jaw.

As more particularly shown in FIG. 14, forceps tip 322 projects axially beyond open end 314 of instrument operating head insertion member 308. It should be noted that the term "forceps tip" is used herein in conjunction with reference number 322 to enable a direct comparison with above-described forceps tip 234 (FIG. 10), even though the described forceps tip 322 does not actually resemble the tip of a conventional forceps.

Shown comprising forceps tip 322 are respective upper and lower gripping jaws 346 and 348. Lower jaw 348 is substantially flat and is directed parallel to handle axis 312, having a rearward end region 350 fixed to a lower region of tubular insertion member 308.

Forceps tip upper jaw 346 is generally C-shaped and has a lower end region 352 pivotally mounted, by a pivot pin 354, to a lower region of member 308. A distal end 356 of forceps control rod or pin 340 is pivotally attached, by a pivot pin 358, to an upper, central region of upper jaw 346.

When control rod 340 is moved in an axial direction away from forceps tip upper jaw 346 (direction of Arrow "D", FIG. 14) by switch 334 (FIGS. 12 and 16) of operating and control system 328, the upper jaw is pivoted upwardly (direction of Arrow "E") about pivot pin 354 to or toward the fully-open position indicated by phantom lines.

In contrast, when forceps tip control rod or pin 340 is caused to be moved in an axial direction toward upper jaw 346 (direction of Arrow "D'", FIG. 14) by operating and control system switch 334, the upper jaw (if open) is pivoted downwardly (direction of Arrow "E'") about pivot pin 354 to or toward its closed position (shown in solid lines).

This described opening and closing movement of upper jaw 346 enables forceps tip 322 to grip an IOL fixation loop region 360 (depicted in phantom lines in FIG. 14) that is supported on an upper surface 362 of forceps tip lower jaw 348 (also as more particularly described below).

As shown, a free, distal end 364 of lower jaw 348 extends a distance, $d_4$, of about 0.20 mm beyond upper jaw 346 for facility of operation, as described below.

Figure 18A:
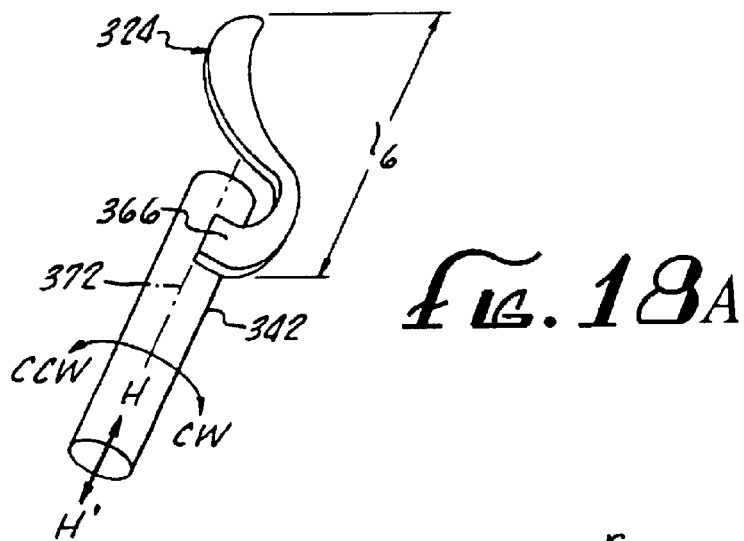
FIG. 18A depicting an offset, axial, helical needle tip.

As shown in FIG. 15, a proximal end 366 of needle tip 324 that projects beyond open end 314 of insertion member 308 is attached in an offset manner (as depicted in FIG. 18A) to a distal end region 368 of needle tip control rod or pin 342.

By way of specific example, with no limitation thereby intended or implied, needle tip 324 preferably has a length, $l_6$, of about 1.0 mm, and has a helical or "corkscrew" shape in a longitudinal direction. Needle tip 324 is preferably offset a distance, $d_5$, of about 0.9 mm from a longitudinal axis 372 of control rod 342 (see also FIG. 18A).

Needle tip control rod 342 is loosely or slidably disposed through a short axial tubular member 376, having a length, $l_7$, of about 10 mm. Tubular member 376 is pivotally connected by an axially-separated pair of links 380 to a proximal insertion member region 382 having a diameter, $D_7$, of about 10 mm (FIG. 13). Links 380 are shown pivotally mounted at each end by pivot pins 384 to respective inner and outer brackets 386 and 388 (FIG. 13) fixed respectively to tubular member 376 and insertion member region 382. Outer brackets 388 are detachably attached to outer member region 382 by screws 389 (FIG. 13).

The proximal end region of tubular member 376 is connected by an offsetting element 392 to a distal end of control rod or pin 344. It can thus be seen from FIG. 15 that when control rod or pin 344 connected to tubular member 376 is caused to be moved axially toward needle tip 324 (direction of Arrow "F") by switch 336 of operating and control system 328, links 380 are caused to pivot upwardly (direction of Arrow "G"). Such upward pivoting of links 380 lifts or pulls up tubular member 376 with its enclosed needle tip control rod or pin 342 and attached needle tip 324 a distance, $d_6$, of about 0.7 mm to an needle tip iris tissue lifting position (shown in broken lines).

In a reverse action, when control rod or pin 344 attached to inner tubular member 376 is caused to be moved axially away from needle tip 324 (direction of Arrow "F'") by switch 336, links 380 are caused to pivot back downwardly (direction of Arrow "G'"). Such downward pivoting motion of links 380 causes the lowering of needle tip control rod or pin 342 and attached needle tip 324, to or toward the tissue-penetrating needle tip position shown in solid lines.

It is to be appreciated that needle tip rod or pin 342 remains free to rotate and move axially within tubular member 376. Thus, rod or pin 342 and attached needle tip 324 connected thereto can, during the iris fixation of an iris fixated IOL, rotated in either the clockwise (CW) direction or the counterclockwise (CCW) direction and moved axially (in the direction of Arrow "H" or "H'") in tubular member 376 by operating and control system switch 338 (FIGS. 12 and 16).

Forceps tip 322 and needle tip 324 can also be selectively moved, in unison, in a forward, extending direction (direction of Arrow "J") or a rearward, retracting direction (direction of Arrow "J'") with insertion member 308 by operating and control system switch 332 (FIGS. 12 and 16), as more particularly described below. Such extension/retraction axial movement of forceps tip 322 and needle tip 324 enables an operator of instrument 300 to adjust the axial positional of the tips as may be desired or needed for accurate fixation position of an iris fixated IOL.

Shown in the electrical schematic drawing of FIG. 16 further comprising operating and control system 328, in addition to previously-mentioned switches 332–338 and battery 330 (which may be a conventional 1.5 volt battery), are respective first, second, third and fourth combination reversible motors and reduction gears (transmissions) 390, 392, 394 and 396.

Forceps tip and needle tip extension and retraction control switch 332 is shown connected to battery 330 by a wire 398 and by electrical wires 400 and 402 to motor and transmission 390 to cause forward and reverse operation of the motor.

In a similar manner, forceps tip opening and closing control switch 334 is connected to battery 330 by a wire 404 and by electrical wires 406 and 408 to motor and transmission 392 to cause forward and reverse operation of the motor.

Needle tip raising and lowering switch 336 is, in turn, shown connected to battery 330 by wires 404 and 410 and by electrical wires 412 and 414 to motor and transmission 394 to cause forward and reverse operation of the motor.

Finally, needle tip rotational and axial movement control switch 338 is shown connected to battery 330 by a wire 420 and by electrical wires 422 and 424 to motor and transmission 396 to cause forward and reverse operation of the motor.

Forceps tip and needle tip motor and transmission 390 is connected, through respective rack and pinion gears 430 and 432 and a drive rod 434 to an axially movable, internal, motor and switch housing 436. In turn, internal housing 436 is connected, through separation portion 305 to insertion member 308 (not shown in FIG. 16), to thereby enable selective forward or rearward movement of forceps tip 322 and needle tip 324 in unison (as described above), by operation of switch 332.

Forceps tip motor and transmission 392 is connected, through respective rack and pinion gears 440 and 442 to a forceps tip connector pin or rod 341, that is detachably connected to forceps tip control pin or rod 340, to thereby enable selective opening and closing of forceps tip 322 (as described above), by operation of switch 334.

In turn, needle tip motor and transmission 394 is connected, through respective rack and pinion gears 444 and 446 to a needle tip tubular member connector pin or rod control rod or pin 345, that is detachably connected to needle tip raising/lowering control pin or rod 344, to thereby enable raising and lowering of needle tip 324 (as described above), by operation of switch 336.

Finally, needle tip rotation and axial movement motor and transmission 396 is connected, through respective worm gears 450 and 452 to a needle tip connector pin or rod 343, that is detachably connected to needle tip control pin or rod 342. Worm gears 450 and 452 are configured for enabling simultaneous CW and limited axial outward movement or CCW rotation and simultaneous axial inward movement of needle tip 324 (as described above), by operation of switch 338.

As shown in FIG. 16, all components of operating and control system 328, except battery 330, switch 322 and associated motor and transmission 390, gears 430 and 432 and rod 434, are installed in internal housing 436 so as to move axially therewith by operation of switch 332.

Although electrical operating and control system 328 described above relative to FIG. 16 will ordinarily be preferred for ease of precise operation of forceps tip 322 and needle tip 324, FIG. 17 depicts a non-electrical (i.e., entirely mechanical) variation operating and control system 328a. System 328a is in all respects the mechanical equivalent of electrical operating and control system 328 and may, for some situations, be preferred.

In mechanical system 328a, that is installed in an instrument handle portion 306a, a thumb-wheel 390a replaces or is used in lieu of needle tip and forceps tip extension and motor and transmission 390 and switch 332 of system 330. A thumb-wheel 392a replaces or is used in lieu of forceps tip opening and closing motor and transmission 392 and switch 334. A thumb-wheel 394a replaces or is used in lieu of needle tip raising and lowering motor and transmission 394 and switch 336. A thumb-wheel 396a replaces or is used in lieu of needle tip rotation motor and transmission 396 and switch 338. Thumb-wheels 390a, 392a, 394a and 396a project through handle portion 306a for operational purposes.

In mechanical operating and control system 328a, battery 330 and all associated electrical wiring depicted in FIG. 16 for electrical operating and control system 330 are, of course, eliminated.

FIG. 18 depicts, for illustrative purposes, with no limitation being thereby intended or implied, several variations of enclavation needle tip configurations that the present inventor has determined may be useful in conjunction with instrument 300 for engaging iris tissue and lifting the engaged iris tissue into pincer gap 490. FIG. 18A shows above-described axial helical needle tip 324 as having the above-described length, $l_6$, of about 1 mm and as having a sidewardly offset distance, $d_7$, from control rod longitudinal axis 372 of about 0.4 mm.

Figure 18B:
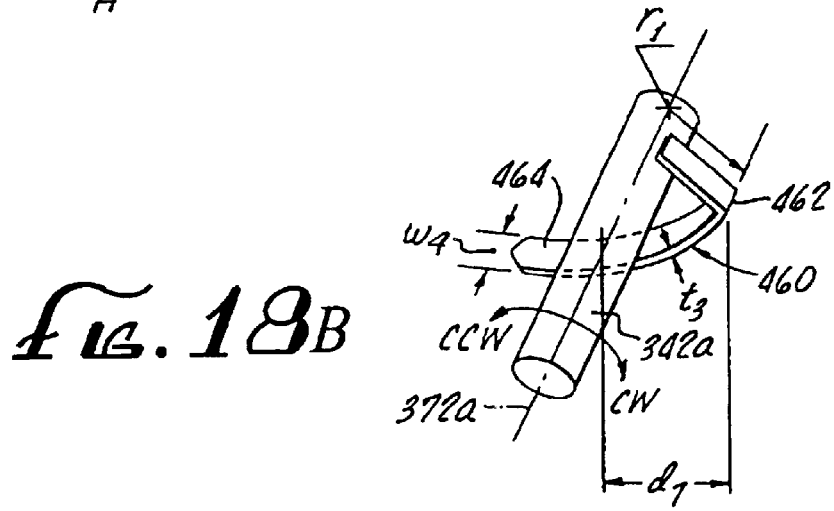
FIG. 18B depicting an arcuate, sidewardly-extending offset needle tip.

FIG. 18B shows a first variation, arcuate needle tip 460 that has a radius of curvature, $r_1$, equal to about 0.9 mm, and that is curved through about 90o. Needle tip 460 has a generally uniform width, $w_4$, of about 0.3 mm and tapers from a thickness, $t_3$, of about 0.15 mm at an attachment end 462, to a knife-edge at a free, pointed end 464. Tip attachment end 462 is offset in a horizontal direction from needle tip control rod longitudinal axis 372a the distance, $d_7$, (i.e., about 0.4 mm).

Figure 18C:
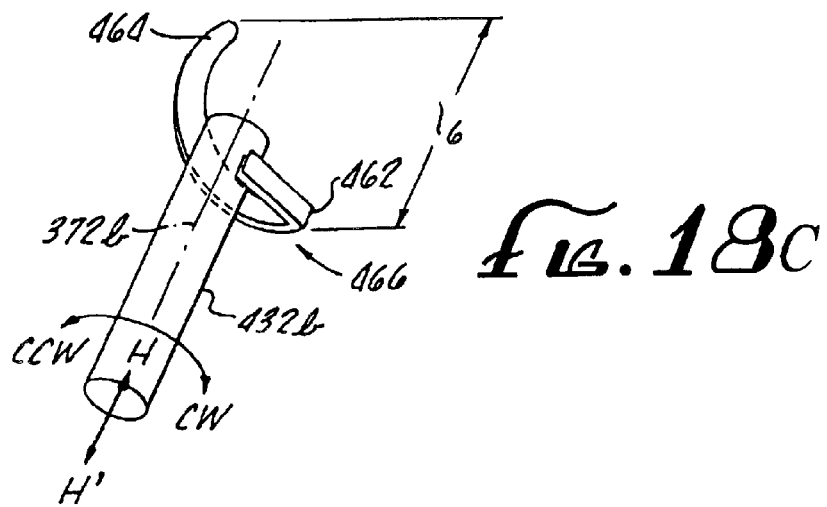
FIG. 18C depicting a forwardly directed, spiral needle tip similar to the needle tip depicted in FIG. 18A.

Shown in FIG. 18C is a second variation needle tip 466 that is similar in some respects to both needle tips 324 and 460 (FIGS. 18A and 18B). Needle tip 466, which is curved similar to needle tip 460, spirals forwardly in a manner similar to helical needle tip 324.

All of needle tips 324, 460 and 466, as well as all variations thereof, are preferably constructed from surgical-grade stainless steel or other strong, biocompatible material and may utilize diamond tips for optimum wear characteristics.

It is important to note that for needle tips 324 (FIG. 18A) and 466 (FIG. 18C) associated gears 450 and 452 (FIGS. 16 and 17) are configured for causing simultaneous needle tip rotational movement and axial movement. For needle tip 460 (FIG. 18B) and other, comparable needle tips-not illustrated), gears 450 and 452 are configured for providing only needle tip rotational movement.

The present inventor has further determined that advantages can be obtained by specifically configuring, as shown in FIGS. 19–21, an IOL fixation loop 478 of a variation iris fixated IOL 480 (similar to iris fixated IOL 20, FIG. 2) to cooperate with operation of above-described combination forceps tip and needle tip instrument 300 (again, as more particularly described below).

Fixation loop 478 corresponds generally to fixation loop 72 depicted in FIG. 2 and described above. As such, fixation loop 478 is formed having respective first and second pincer arms 482 and 484. Respective adjacent ends 486 and 488 of pincer arms 482 and 484 define therebetween a narrow pincer gap 490 (corresponding to above-described pincer gap 78, FIG. 2) preferably having a gap width, $w_5$, of about 0.07 mm.

As depicted in FIG. 21, pincer arm 482, which is representative of pincer 484, is substantially flat and rectangular with rounded corners, having a preferred width, $w_6$, of about 0.35 mm and a preferred thickness, $t_4$, of about 0.15 mm. A fixation loop side region 492 opposite pincer gap 490 is preferably round in cross section, having a diameter, $D_{10}$, of about 0.2 mm.

As shown in FIG. 20, respective lower surfaces 500 and 502 of fixation loop opposite end regions 504 and 506 are flared or offset upwardly a preferred distance, $d_8$, of about 0.15 mm above a plane 510 defined by respective lower surfaces 512 and 514 of pincer arms 482 and 484. Note that plane 510 is also coincident with an iris anterior surface (such as iris surface 22G, FIG. 10) when IOL 480 is fixated to an iris. Such upward offset of end regions 504 and 506 provides clearance for forceps tip lower jaw 348 (FIG. 14), as described below.

Respective target gripping regions 520 and 522 of fixation loop end regions 504 and 506 are preferably thickened by a distance, $d_9$, of about 0.1 mm (FIG. 21). These regions 520 and 522 not only provide thickened regions for right angle gripping by forceps tip 322 during iris fixation of loop 478 (as shown in FIG. 22), but also provide visual guides for enabling accurate right angle positioning of the forceps tip.

FIG. 22 depicts, in a series of four steps, typical operation of combination forceps and enclavation needle instrument 300 in combination with fixation loop 478 of exemplary iris fixated IOL 480. By way of example, instrument insertion member 308 is shown in FIGS. 22A–D in solid lines positioned at a right angle to the long axis of fixation loop 478; however, there is indicated by broken lines in FIG. 22A an alternative positioning of the instrument member designated 308a parallel to the long axis of the fixation loop.

For purposes of describing the fixation loop attachment procedure, with no limitation being thereby intended or implied, electrical operation and control system 328 is assumed.

IOL 480 is first inserted, using known IOL insertion procedures, through an ocular incision (not shown) into the anterior chamber of a patient's eye. Forceps tip 322 and needle tip 324 are then optimally positioned relative to a selected fixation loop 478 (for example, with the aid of visual optics) by the ophthalmic surgeon's manipulation of operating and control switch 332 as described above with respect to FIGS. 12 and 16). As described above with respect to FIGS. 12 and 16, needle tip 324 is elevated by the surgeon to the desired elevation by manipulation of switch 336 and forceps tip 322 is opened by manipulation of switch 334.

Figure 22A:
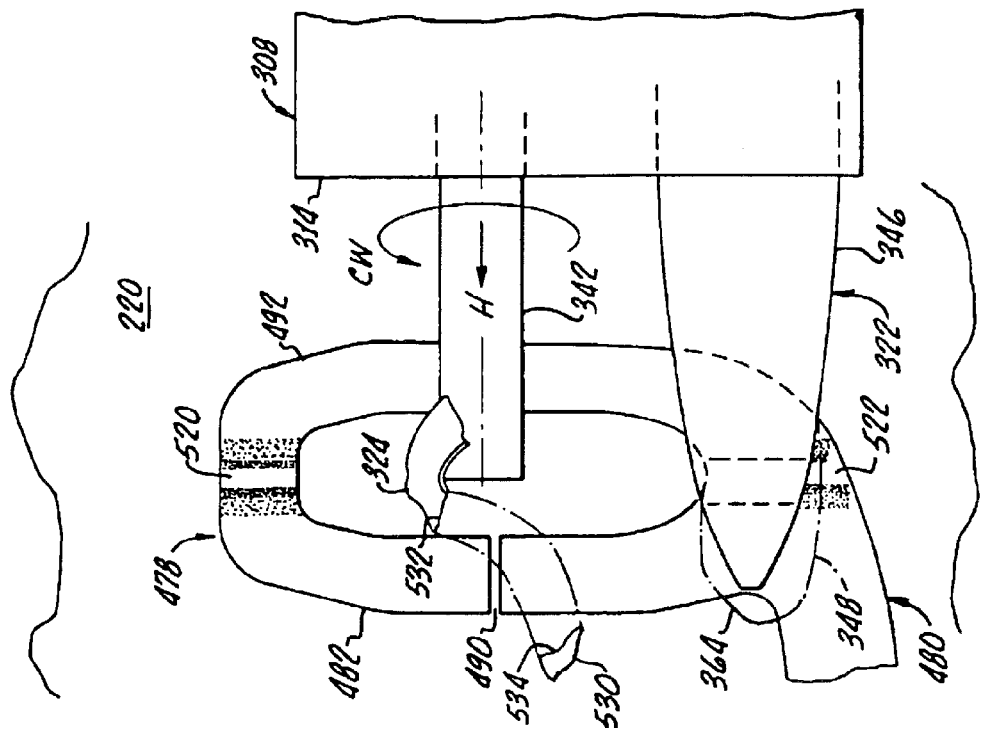
FIG. 22A depicting the forceps tip gripping one of the thickened end regions of the fixation loop to hold the fixation loop against the anterior surface of an iris and with the enclavation needle tip portion positioned above the iris surface inside the fixation loop near the fixation loop pincer arm gap and showing in broken lines an alternative positioning of the forceps tip and needle tip.

Then, as depicted in FIG. 22A by way of example, forceps tip lower jaw 348 is moved into a position beneath raised region 522 of fixation loop 478. Accurate positioning of forceps tip 322 is visually determined by visually observing when lower jaw end 364 becomes visible beyond fixation loop 478 in the region of pincer arm 484, with the loop resting on lower jaw upper surface 362 (see FIG. 14). Switch 334 is then manipulated to close forceps tip upper jaw 346 against fixation loop region 522 (see also FIG. 14).

Needle tip 324 is configured so that at the above-described fixation loop gripping position of forceps tip 322, a sharp needle tip distal end 530 is positioned above a desired iris tissue engagement point within fixation loop 478 and adjacent to and in alignment with pincer gap 490. Needle tip 324 is then lowered (not shown), by operation of switch 336, until needle tip distal end 530 touches iris anterior surface 220 (FIG. 22A).

Figure 22B:
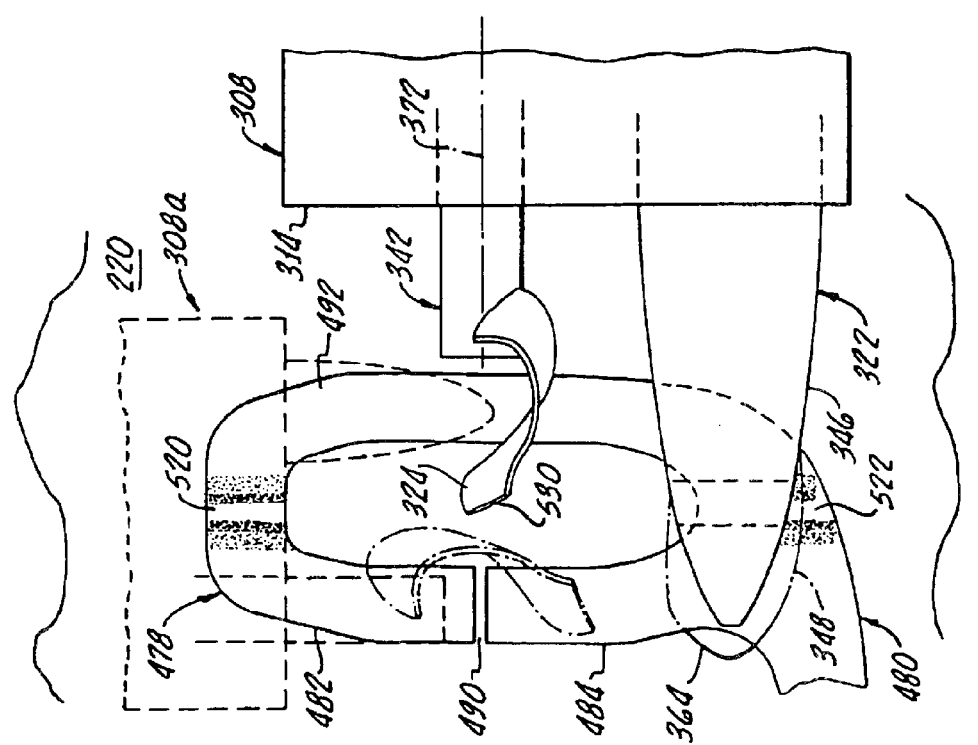
FIG. 22B showing the forceps tip still holding the fixation loop against the iris surface and depicting the helical needle tip advanced in the direction of Arrow "E" and partially rotated in the CCW direction to insert the needle tip beneath the iris surface diagonally under the pincer arm gap.

As next depicted in FIG. 22B (with fixation loop 478 held against iris anterior surface 220 by forceps tip 322), needle tip 324 is partially rotated in the clockwise (CW) direction by operation of switch 338. Such partial rotation of needle tip 324 causes needle tip distal end 530 to penetrate the iris stromal tissue at a narrow entry or engagement line 532. Continued partial CW rotation of needle tip 324 with simultaneous advancement of the needle tip (in the direction of Arrow "H") causes the needle tip to spiral through the engaged iris stromal tissue beneath pincer gap 490 until needle tip distal end 530 subsequently exits the iris tissue at a narrow exit line 534. As described above, in unison with such CW partial rotation of needle tip 324, the needle tip is advanced (by the same operation of switch 338) out of open end 314 of tubular member 308.

Figure 22D:
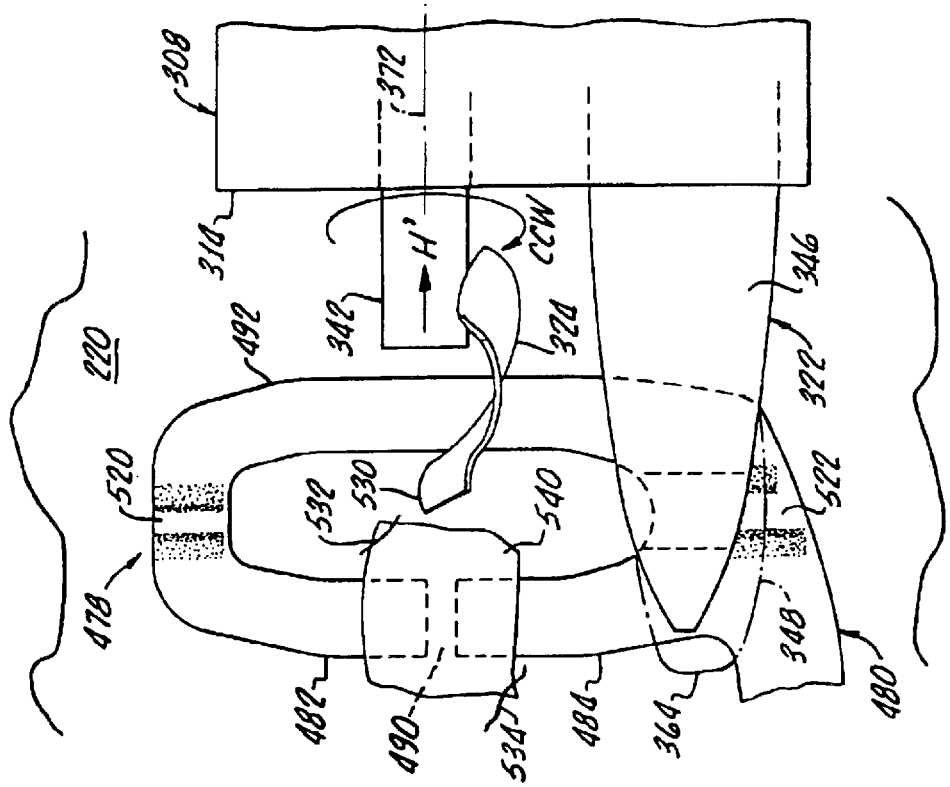
FIG. 22D depicting the needle tip partially rotated back in the CW direction and retracted in the direction of Arrow "E'" to thereby withdraw the needle tip from the engaged iris tissue, leaving the previously uplifted region of iris tissue pinched (i.e., trapped) in the pincer arm gap.
Figure 22C:
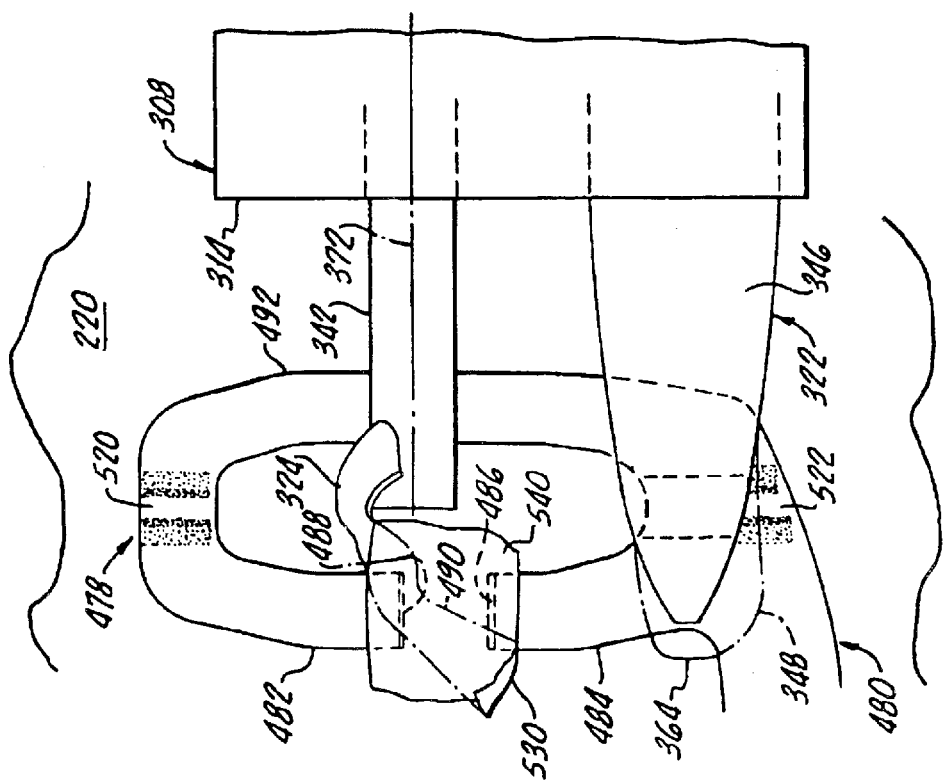
FIG. 22C being similar to FIG. 22B, but depicting further CCW rotation of the needle tip to lift the engaged iris tissue into the pincer arm gap that is also lifted and widened by the lifted iris tissue.

In the next operational step illustrated in FIG. 22C with forceps tip 322 still gripping fixation loop 482 and holding the fixation loop against iris anterior surface 220 as described above, and with needle tip 324 still embedded in iris stromal tissue beneath pincer gap 490, the needle tip is lifted (not shown) by operation of switch 336. This lifting of needle tip 324 lifts an iris stromal tissue region 540 into pincer gap 490, thereby lifting and spreading respective ends 486 and 488 of pincer arms 482 and 484 and widening the pincer gap.

Finally, as depicted in FIG. 22D, needle tip 324 is rotated back in the counterclockwise (CCW) direction by operation of switch 338. This operation of switch 338 simultaneously moves (i.e., retracts) needle tip 324 rearwardly (direction of Arrow "H'"), leaving tissue region 540 pinched or trapped in the resulting closing of pincer gap 490 as pincer arms 482 and 464 flex back downwardly toward their original, unflexed position.

At this point, the selected fixation loop 478 has been attached to iris anterior surface 220. Needle tip 324 is then lifted, by operation of switch 336 to clear side 492 of fixation loop 478 and forceps tip upper jaw 346 is opened by operation of switch 334. Instrument 300 may then be repositioned to repeat the above-described attachment procedure on the second fixation loop.

The present inventor considers that the ability to easily and quickly separate the above-described operating head portion 304 (with forceps tip 322 and needle tip 324) from the rest of instrument 300 is desirable (but not essential). Such separation of operating head portion 304 is advantageous for reasons as enabling: (i) the rapid installation of a sterilized operating head portion 304 before each new use of instrument 300, (ii) the efficient sterilization of operating head portion 304, and (iii) the easy replacement of a damaged or worn needle tip 324 and/or forceps tip 322.

Disconnection and reconnection of operating head portion 304 relative to the rest of instrument 300 is provided by detachable connections (described below) between control pins or rods 340, 342 and 344 and their associated connecting pins or rods 341, 343 and 345 and between outer tubular member region 382 and inner housing 436 (FIG. 16).

These detachable connections are identical for each interconnecting pair of control and connecting pins or rods 340 and 341, 342 and 343, and 344 and 345. Consequently, only the detachable connection of a representative pair of control and connecting pins or rods 340 and 341 (for opening and closing forceps tip 322) is depicted in FIGS. 23–26 and described hereinbelow.

Figure 23:
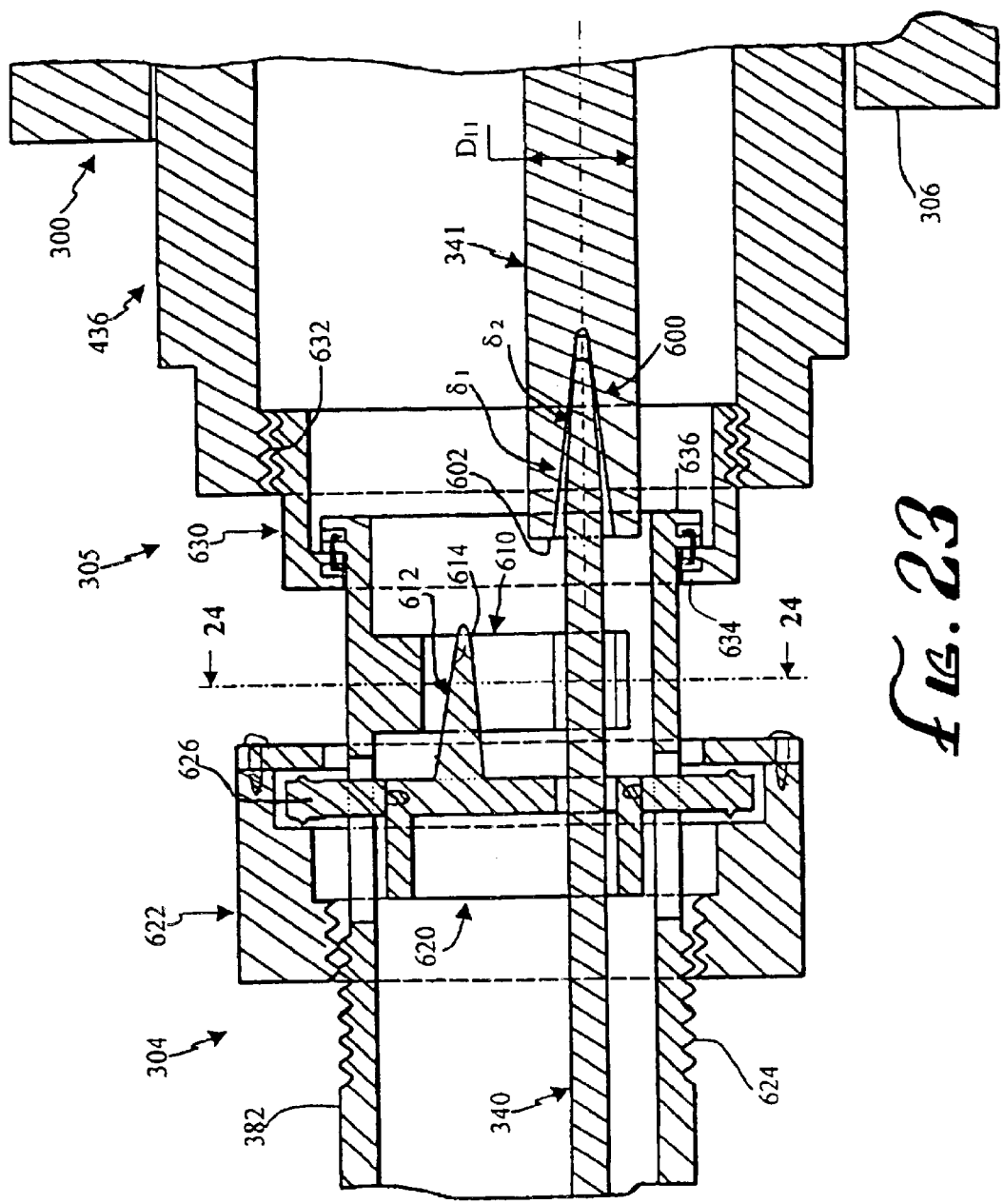
FIG. 23 is a longitudinal cross sectional drawing looking along line 23—23 of FIG. 12 showing internal features of the separation portion of the combination instrument and showing, by way of representative example, the forceps tip control pin frictionally connected to its associated connector pin.
Figure 24:
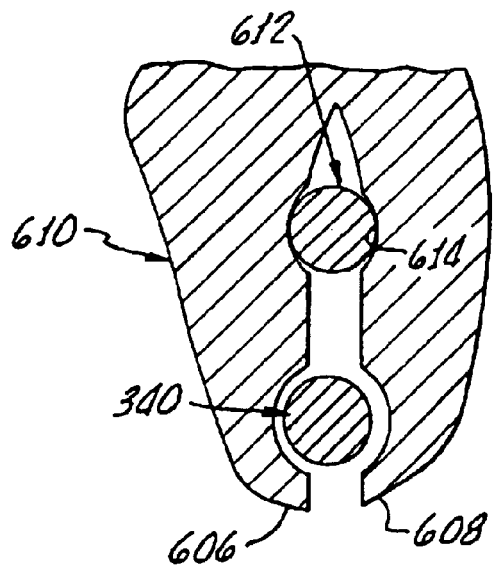
FIG. 24 is a transverse cross sectional drawing looking along line 24—24 of FIG. 23 showing the associated clamping member for the forceps tip control pin in an unclamped configuration.

FIG. 23, thus depicts the detachable connection between control pin or rod 340 and associated connecting pin or rod 341, as is required for the controlled opening and closing of forceps tip 322 (not shown) by operation of switch 334 (see FIG. 16). For such detachable connection, a blunt, conical, proximal end 600 of forceps tip control pin or rod 340 is frictionally received or fit into a conically tapered recess or socket 602 formed in a distal end region of connecting pin or rod 341. Preferably, conical proximal end 600 of control pin or rod 340 is tapered at an angle, $\delta_2$, of about 7° and recess 602 is tapered at an angle, $\delta_2$, of about 10°. Connecting pin or rod 341 may have a diameter, $D_{11}$, that is about 2 mm.

With the above-described frictional connection made between control pin or rod 340 and associated connecting pin or rod 341, the control pin or rod can be moved axially by connecting pin or rod 341. However, to permit axial movement of control pin or rod 340, respective first and second jaws 606 and 608 of a spring-loaded control pin clamp 610 (FIG. 24) are held in an open, non-pin gripping position by an axially directed, tapered pin 612 inserted into a mating tapered aperture 614 in the clamp, as shown in both FIGS. 23 and 24.

Tapered pin 612 projects axially rearward from a circular member 620 (as do two hidden, identical tapered pins associated with the two other pairs 342, 343 and 344, 345 of control and connecting pin or rods (also not shown). An internally threaded retaining ring 622 tightened on an externally threaded region 624 of tubular member region 382 maintains (through a circular flange 626 on circular member 620) tapered pin 612 in clamp aperture 614 to hold clamp jaws 606 and 608 open, thereby enabling free axial movement of control pin or rod 340.

An externally threaded ring 630 is threaded into an internally threaded end 632 of internal housing 436. An inwardly-directed flange 634 of ring 630 retains tubular member region 382 in place by bearing against an outwardly-directed flange 636 at the proximal end of member region 382.

Figure 26:
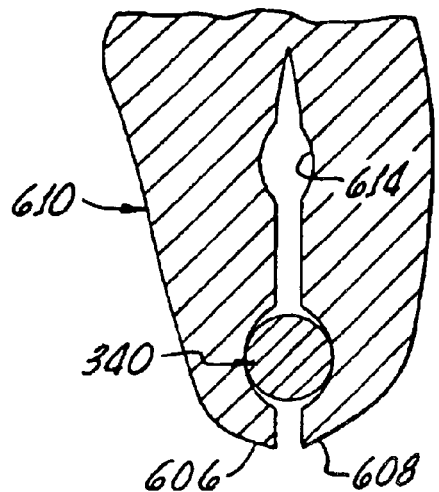
FIG. 26 is a transverse cross sectional drawing looking along line 26—26 of FIG. 25 showing the associated clamping member clamping the forceps tip control pin.
Figure 25:
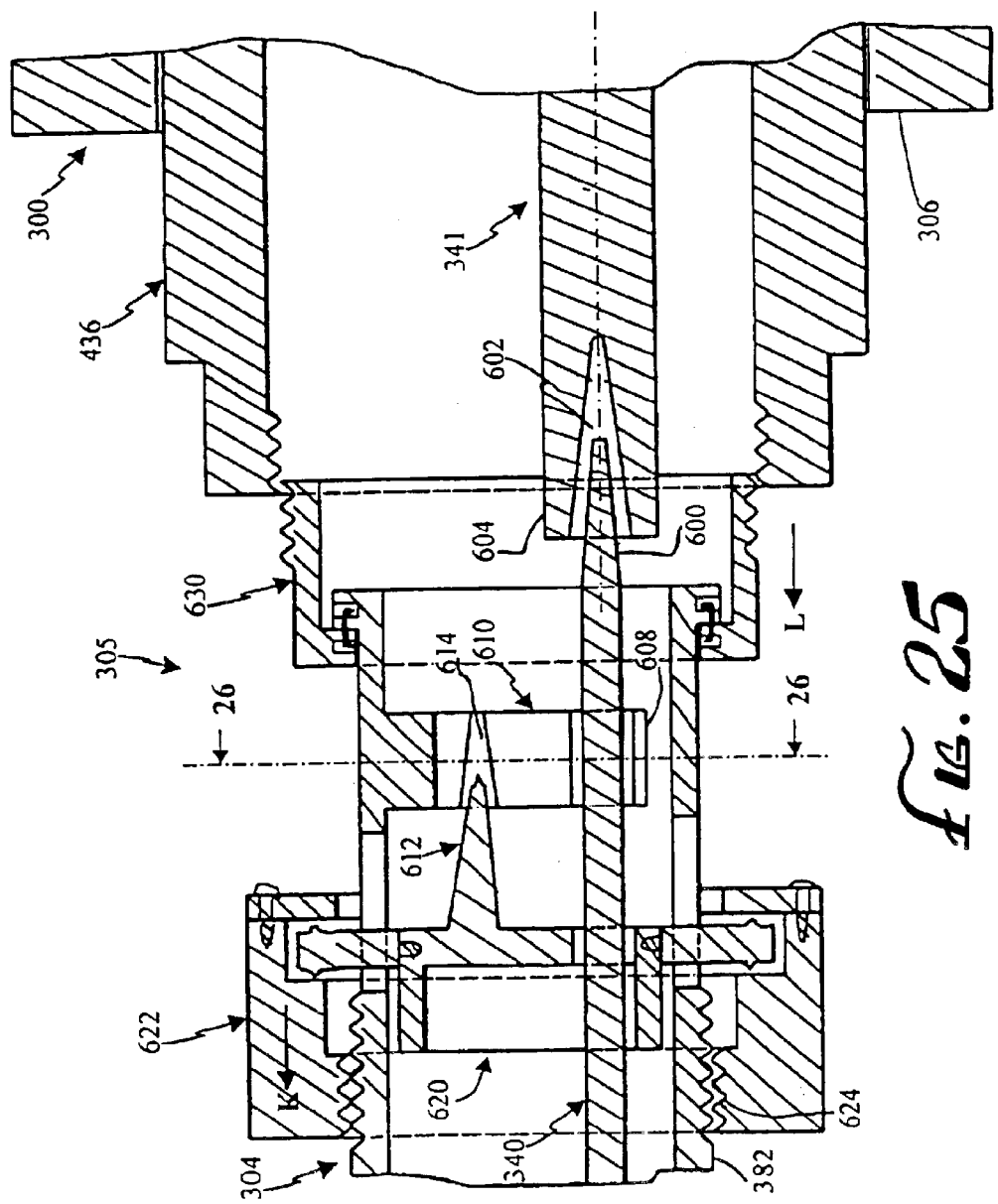
FIG. 25 is a longitudinal cross sectional drawing similar to FIG. 23, but showing the representative control pin clamped by the pin clamping member depicted in FIG. 24 and showing the control pin disconnected from its associated connector pin.

The procedure for detachment of insertion portion 304 from internal housing 436 is made obvious from a consideration of FIGS. 25 and 26 and comprises the steps set forth below.

Forceps tip 322 and needle tip 324 are first returned to an initial "zero" or "null" position, by appropriate operation of switches 332, 334, 336 and 338.

Internally threaded ring 622 is then screwed forwardly (direction of Arrow "K") on externally threaded region 624 of tubular member region 382. This forward movement of ring 622 pulls tapered pin 614 (through corresponding forward movement of member 620) out of clamp aperture 614. This permits clamp jaws 606 and 608 to close in a gripping relationship against control rod or pin 340 (FIG. 26). (In the same manner and at the same time, corresponding clamps are clamped against control pins or rods 342 and 344—not shown.) Externally threaded ring 630 is next unscrewed forwardly (direction of Arrow "L") from internally threaded end 632 of housing 436 to complete the forward separation of insertion portion 304 from housing 436 and thus instrument barrel 306. Note that the clamping by clamp 610 of control pin or rod 340 enables the control pin or rod conical end 600 to be pulled free from connecting pin or rod tapered recess 602 when insertion portion 304 is pulled forwardly from housing 436.

Preferably all above-described parts of insertion portion 304 are constructed of a surgical grade of stainless steel to enable the separated insertion portion to be sterilized by conventional sterilization procedures.

Connection of the same (or another) insertion portion 304 to internal housing 436 is performed by reversing the above-described separation steps.

Figure 27:
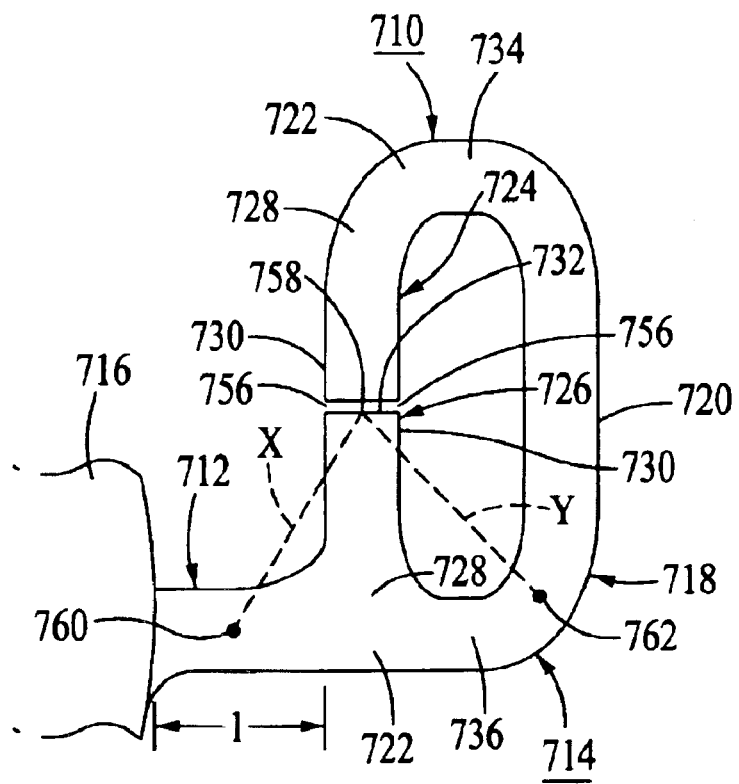
FIG. 27 is a detail view of an alternative modified haptic fixation loop having features of the invention.

FIG. 27 illustrates a fixation member 710 similar to the IOL fixation loop 478 which is illustrated in FIG. 19. In the embodiment illustrated in FIG. 27, the fixation member 710 has at least one connecting element 712 and a pincer element 714. The connecting element 712 is attached to an optic 716 and the pincer element 714 is attached to the connecting element 712. The pincer element 714 comprises (i) a side region 718 having a central portion 720 and opposed end portions 722 and (ii) a first pincer arm 724 and a second pincer arm 726 attached to the side region 718. Both the first pincer arm 724 and the second pincer arm 726 have a first end 728 and a second end 730. The first ends 728 of the two pincer arms 724 and 726 are attached to the side region 718 and the second ends 730 of the two pincer arms 724 and 726 are unattached and disposed proximate to, but spaced apart from, one another, so as to form a narrow pincer gap 732. In the embodiment illustrated in FIG. 27, the respective target gripping regions 734 and 736 of the fixation member are not thickened as are the gripping regions 520 and 522 of the of the fixation loop 478 illustrated in FIG. 19. The gripping regions 734 and 736, however, may be thinned as they are in the embodiments illustrated in FIGS. 30 and 31.

In the embodiment illustrated in FIG. 27, the connecting elements 712 are quite short. In a typical embodiment, each of the connecting elements 712 has a length l less than about 1.0 mm. In a most typical embodiment, the length l of each connecting element 712 is about 0.7 mm. The short length of the fixation members 712 enhances the implantation of the lens 740 by folding techniques because the short fixation members 710 minimize the range of movement during the implantation unfolding. This results in less chance of corneal endothelial cell damage.

FIG. 27 also illustrates a very important features of the embodiments illustrated in FIGS. 27, 28 and 30–36. As can be seen in FIG. 27, each pincer gap 732 has opposed end portions 756 and a central-most portion 758. Each fixation member 710 has a first location 760 disposed closer to the optic 716 than the pincer gap 732. This first location 760 is spaced apart from the central-most portion 758 of the pincer gap 732 by a distance x which is typically between about 1.3 mm. Each fixation member 710 further has a second location 762 disposed farther from the optic 716 than the pincer gap 732. This second location 762 is spaced apart from the central-most portion 758 of the pincer gap 732 by a distance y, which is substantially the same distance as x.

The first location 760 and the second location 762 provide gripping sites for the forceps of a combination installation instrument comprising an enclavation needle and a forceps instrument, such as described above. Because there are two such gripping locations, one disposed closer to the optic 716 than the pincer gap 732 and one disposed further from the optic 716 than the pincer gap 732, the practitioner can install both of the two fixation members 710 to the eye of a patient using a single combination instrument. A practitioner does not have to own and maintain two separate combination instruments, each having a different orientation of the enclavation needle and the forceps. A single instrument, having any one such orientation, can be employed by the practitioner to fix both haptics, because both fixation members 710 have alternative gripping sites (the first location 760 and the second location 762) which will allow gripping of the fixation member 710 by the forceps portion of the instrument from either side.

Figures 28, 29:
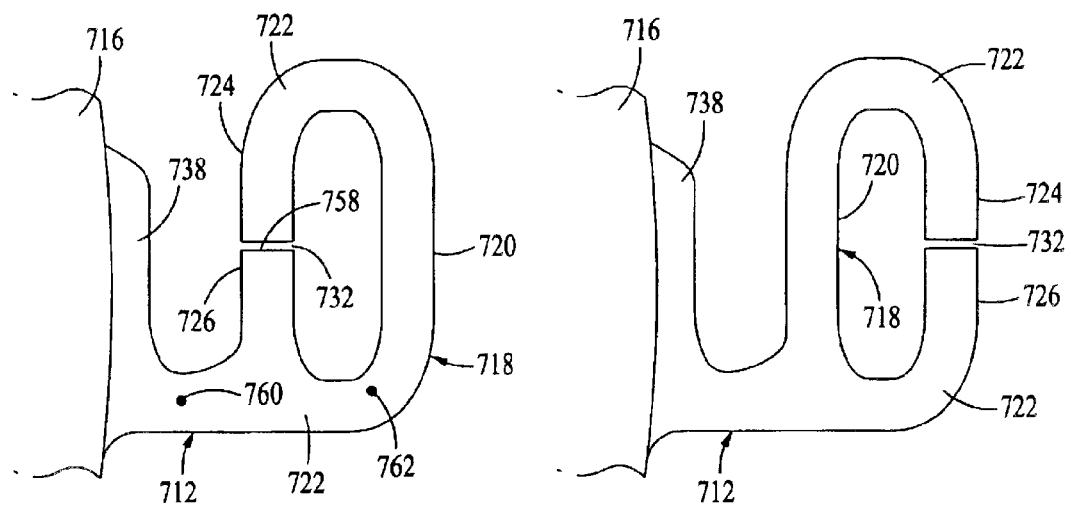
FIG. 28 is a detail view of a second alternative modified haptic fixation loop having features of the invention.
FIG. 29 is a detail view of a third alternative modified haptic fixation loop having features of the invention.

FIG. 28 illustrates an alternative IOL fixation member 710. Unlike the fixation member 710 illustrated in FIG. 27, the embodiment illustrated in FIG. 28 has a connecting element 712 with a widened attachment portion 738 which is disposed in tangential abutment to the optic 716. Such widened attachment portion 738 is useful in providing improved stability to the optic 716 during implantation by minimizing its tendency to "tilt."

FIG. 29 illustrates an alternative embodiment to that which is illustrated in FIG. 28. Contrary to the embodiment illustrated in FIG. 28 wherein the pincer arms 724 and 726 are disposed between the optic 716 and the central portion 720 of the side region 718, in the embodiment illustrated in FIG. 29, the central portion 720 of the side region 718 is disposed between the optic 716 and the pincer arms 724 and 726.

FIG. 30 illustrates an alternative iris fixated intraocular lens 740. In the intraocular lens 740 illustrated in FIG. 30, the two fixation members 710 are wholly disposed on opposite sides of the optic 716. Like the embodiment illustrated in FIG. 27, the connecting elements 712 are also quite short. In a typical embodiment, each of the connecting elements 712 has a length l less than about 1.0 mm. In a most typical embodiment, each of the connecting elements 712 has a length l of about 0.7 mm. The short length of the fixation members 712 enhances the implantation of the lens 740 by folding techniques because the short fixation members 710 minimize the range of movement during the implantation unfolding. This results in less chance of corneal endothelial cell damage. The width of each fixation member 710 is typically about 2.4 mm.

In the embodiment illustrated in FIG. 30, the side regions 718 of both of the two fixation members 712 comprise a first transverse member 742. The first transverse member 742 of both fixation members 712 are disposed substantially along the same line 744. Also in the embodiment illustrated in FIG. 30, both of the fixation members 712 comprise an orthogonal member 746 disposed substantially perpendicular to the first transverse member 742. A second transverse member 748 is attached to the orthogonal member 746 and disposed substantially parallel to the first transverse member 742.

The embodiment illustrated in FIG. 30 has a significant advantage over the embodiments illustrated in FIGS. 27 and 28. In the embodiments illustrated in FIGS. 27 and 28, the first location 760 is disposed along the connecting element 712. As can be seen in FIG. 31, the connecting elements 712 are typically disposed along the "vaulting" portion of the fixation member 710, that is, along the transition between the plane in which the optic 716 is disposed and the plane in which the pincer element 714 is disposed. The vaulting portions of fixation members 710 in most IOL's are, for strength purposes, not flat. Accordingly, in embodiments such as illustrated in FIGS. 27 and 28, wherein the first location 760 is disposed along the vaulting portion, the gripping by the forceps portion of a combination instrument at the first location 760 can be somewhat difficult. The embodiment illustrated in FIGS. 30–33 and 35 eliminates this problem by disposing both the first location 760 and the second location 762 on now-vaulted, flat portions of the pincer element 714. In FIGS. 30–33 and 35, this is facilitated by use of an extension portion 764 which is provided along the second transverse member 748. The extension portion 764 extends the second transverse member 748 beyond the pincer arm 726. The extension portion 764 is used to accommodate either the first location 760 or the second location 762.

In the embodiment illustrated in FIG. 30, the pincer arms 724 and 726 are disposed between the optic 716 and the central portion 720 of the side region 718. This is also the case with respect to the embodiments illustrated in FIGS. 32–34. However, in alternative embodiments, such as those illustrated in FIGS. 35 and 36, the central portion 720 of the side region 718 is disposed between the optic 716 and the pincer arms 724 and 726.

As illustrated in FIG. 31, the transverse members 742 and 748 of the fixation members 710 can have an internal depression 750 on the forward face of the second transverse member 748. The internal impression 750 improves the elasticity of the transverse members 742 and 748 to bending of the pincer element 714. The internal impression 750 also limits forceps contact outside of the internal impression 750.

Typically, the optic 716 and the connecting elements 712 are made of different materials having different coefficients of expansion. In the embodiment illustrated in FIG. 32, the juncture between the optic 716 and the connecting elements 712 has a pair of holes 754. These holes 754 reduce contact between the different materials of the optic 716 and the connecting elements 712 and minimize uneven expansion problems at the juncture between the optic 716 and the connection elements 712.

Figure 33:
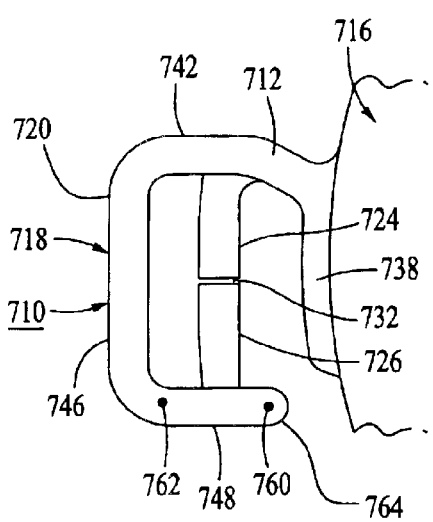
FIG. 33 is a detail view of a haptic portion of an intraocular lens having features of the invention.

FIG. 33 is a detail illustration of a fixation member 710 similar to the fixation member 710 used in the embodiment illustrated in FIG. 30. In the embodiment illustrated in FIG. 33, however, the connecting element 712 is reduced in mass to reduce the impact of optic folding on the fixation member 710. In a typical embodiment of the fixation member 710 as illustrated in FIG. 33, the width of the first transverse member 742 is about 0.30 mm, the width of the orthogonal 746 is typically about 0.20 mm and the width of the second transverse member 748 is typically about 0.30 mm. Also in the embodiment illustrated in FIG. 33, the width of the pincer arms 724 and 726 is typically about 0.35 mm, and the total length of the two pincer arms 724 and 726 (including the width of the pincer gap 732) is about 1.70 mm. Typically, the distance between the pincer arms 724 and 726 and the widened attachment portion 738 of the connecting elements 712 is at least about 0.55 mm. The width of the widened attachment portion is typically less than about 0.35 mm.

Figure 34:
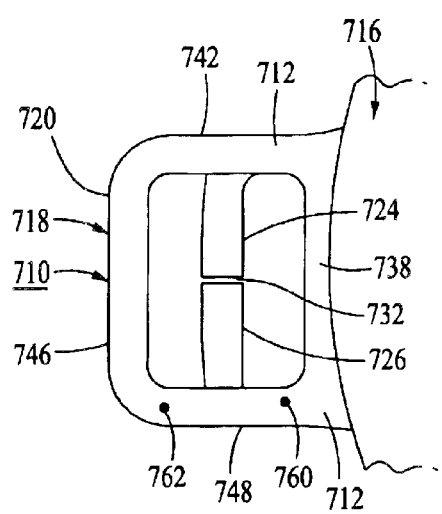
FIG. 34 is a detail view of a second haptic portion of an intraocular lens having features of the invention.

In the embodiment illustrated in FIG. 34, each fixation member 710 has two connecting elements 712. The use of two connecting elements 712 adds additional rigidity and stability to the fixation member 710.

Figure 35:
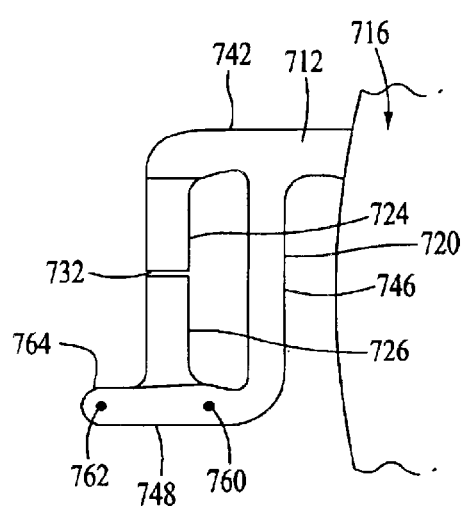
FIG. 35 is a detail view of a third haptic portion of an intraocular lens having features of the invention.

The embodiment illustrated in FIG. 35 is similar to the embodiment illustrated in FIG. 33. In the embodiment illustrated in FIG. 35, however, the central portion 720 of the side region 718 is disposed between the optic 710 and the pincer arms 732.

Figure 36:
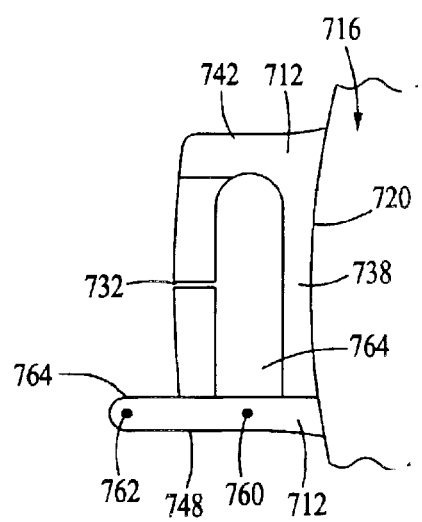
FIG. 36 is a detail view of a fourth haptic portion of an intraocular lens having features of the invention.

Also, the embodiment illustrated in FIG. 36 is similar to the embodiment illustrated in FIG. 34. In the embodiment illustrated in FIG. 36, however, the central portion 720 of the side regions 718 is disposed between the optic 716 and the pincer arms 732.

Although there have been described above an iris fixated IOL and variations thereof, as well as an associated combination enclavation needle and forceps IOL-iris attachment instrument, in accordance with the present invention for purposes of illustrating the manner in which the present invention maybe used to advantage, it is to be understood that the invention is not limited thereto. Consequently, any and all variations and equivalent arrangements which may occur to those skilled in the applicable art are to be considered to be within the scope and spirit of the invention as set forth in the claims which are appended hereto as part of this application.

What is claimed is:

1. An iris fixated intraocular lens comprising:
   (a) an optic having an optical axis, an anterior side and a posterior side; and
   (b) at least two fixation members, each of said fixation members having at least one connecting element and a pincer element, the connecting element being attached to the optic and the pincer element being attached to the connecting element, the pincer element comprising:
      (i) a side region having a central portion and opposed end portions; and
      (ii) a first pincer arm and a second pincer arm attached to the side region, both the first pincer arm and the second pincer arm having a first end and a second end, the first ends of the two pincer arms being attached to the side region and the second end of the two pincer arms being unattached and disposed proximate to, but spaced apart from, one another, so as to form a narrow pincer gap, the pincer gap having a substantially uniform width and being sized for pinching a small surface segment of iris tissue into the pincer gap for detachably attaching the intraocular lens to an iris anterior surface.

2. The intraocular lens of claim 1 wherein each fixation member has only one connecting element.

3. The intraocular lens of claim 1 wherein each connecting element has a widened attachment portion which is disposed in tangential abutment to the optic.

4. The intraocular lens of claim 1 wherein the two fixation members are wholly disposed on opposite sides of the optic.

5. The intraocular lens of claim 1 wherein the central portion of the side region is disposed between the optic and the pincer arms.

6. The intraocular lens of claim 1 wherein:
   (a) both fixation members have only one connecting element;
   (b) the side regions of both of the two fixation members comprise a first end portion attached to the one connecting element and an unattached second end portion;
   (c) each pincer gap has opposed end portions and a central-most portion;
   (d) each fixation member has a first location proximate to the second end portion disposed closer to the optic than the pincer gap, the first location being spaced apart from the central-most portion of the pincer gap by a distance x sufficient to provide a gripping site for a forceps in a combination installation instrument comprising an enclavation needle and a forceps, said distance x being between about 1.0 mm and about 1.7 mm; and
   (e) each fixation member has a second location proximate to the second end portion disposed farther from the optic than the pincer gap, the second location being spaced apart from the central-most portion of the pincer gap by a distance y, where x=y.

* * * * *